(12) United States Patent
DeWitt et al.

(10) Patent No.: US 9,732,031 B2
(45) Date of Patent: Aug. 15, 2017

(54) METHODS OF TREATING NEUROLOGICAL AND OTHER DISORDERS USING ENANTIOPURE DEUTERIUM-ENRICHED BUPROPION

(71) Applicant: DeuteRx, LLC, Andover, MA (US)

(72) Inventors: Sheila DeWitt, Auburn, NH (US); Vincent Jacques, Somerville, MA (US); Leonardus H. T. van der Ploeg, Newton, MA (US)

(73) Assignee: DeuteRx, LLC, Andover, MA (US)

( * ) Notice: Subject to any disclaimer, the term of this patent is extended or adjusted under 35 U.S.C. 154(b) by 0 days.

(21) Appl. No.: 15/103,144

(22) PCT Filed: Dec. 19, 2014

(86) PCT No.: PCT/US2014/071519
§ 371 (c)(1),
(2) Date: Jun. 9, 2016

(87) PCT Pub. No.: WO2015/095713
PCT Pub. Date: Jun. 25, 2015

(65) Prior Publication Data
US 2016/0311757 A1  Oct. 27, 2016

Related U.S. Application Data

(60) Provisional application No. 61/919,155, filed on Dec. 20, 2013.

(51) Int. Cl.
*A61K 31/135* (2006.01)
*C07C 225/10* (2006.01)
*A61K 31/137* (2006.01)

(52) U.S. Cl.
CPC .......... *C07C 225/10* (2013.01); *A61K 31/137* (2013.01); *C07B 2200/07* (2013.01)

(58) Field of Classification Search
CPC .................................................. C07C 225/10
USPC ....................................................... 514/649
See application file for complete search history.

(56) References Cited

U.S. PATENT DOCUMENTS

| 3,819,706 A | 6/1974 | Nariman |
| 6,221,335 B1 | 4/2001 | Foster |
| 6,440,710 B1 | 8/2002 | Keinan et al. |
| 6,603,008 B1 | 8/2003 | Ando et al. |
| 7,517,990 B2 | 4/2009 | Ito et al. |
| 8,524,780 B2 | 9/2013 | Czarnik |
| 8,735,454 B2 * | 5/2014 | Czarnik ................ C07C 225/16 514/649 |
| 2007/0082929 A1 | 4/2007 | Gant et al. |
| 2007/0197695 A1 | 8/2007 | Potyen et al. |
| 2009/0076161 A1 | 3/2009 | Czarnik |
| 2010/0075950 A1 * | 3/2010 | Gant ..................... C07B 59/001 514/211.13 |
| 2014/0018436 A1 | 1/2014 | Czarnik |

FOREIGN PATENT DOCUMENTS

| WO | WO-95/26325 A2 | 10/1995 |
| WO | WO-99/38499 A2 | 8/1999 |
| WO | WO-99/38502 A1 | 8/1999 |
| WO | WO-99/38503 A1 | 8/1999 |
| WO | WO-99/38504 A1 | 8/1999 |
| WO | WO 2009/105218 * | 8/2009 ........... C07C 215/30 |
| WO | WO-2009/105218 A2 | 8/2009 |
| WO | WO-2012/118562 A1 | 9/2012 |

OTHER PUBLICATIONS

Haskins, N. J. "The Application of Stable Isotopes in Biomedical Research," *Biomedical Mass Spectrometry*, 9 (7), 1982, 269-277.
Kushner, D.J. et al. "Pharmacological Uses and Perspectives of Heavy Water and Deuterated Compounds," *Canadian Journal of Physiology and Pharmacology*, 1999, 77(2), 79-88.
Tonn et al. "Simultaneous Analysis of Diphenhydramine and a Stable Isotope Analog ($^{2}H_{10}$)Diphenhydramine Using Capillary Gas Chromatography with Mass Selective Detection in Biological Fluids from Chronically Instrumented Pregnant Ewes," *Biological Mass Spectrometry*, 22 (11) 1993, 633-642.
Wolen, R. L. "The application of stable isotopes to studies of drug bioavailability and bioequivalence," *Journal of Clinical Pharmacology* (26), 1986, 419-424. (Abstract Only).
International Search Report and Written Opinion for PCT/US2014/071519, mailed Feb. 10, 2015 (12 pages).
Shao, L. & Hewitt, M.C. "The Kinetic Isotope Effect in the Search for Deuterated Drugs," *Drug News & Perspectives*, 2010, vol. 23, No. 6, pp. 398-404.

* cited by examiner

*Primary Examiner* — Nizal Chandrakumar
(74) *Attorney, Agent, or Firm* — Goodwin Procter LLP

(57) ABSTRACT

The invention provides enantiopure deuterium-enriched bupropion, pharmaceutical compositions, and methods of treating neurological disorders, movement disorders, cardiovascular disorders, metabolic disorders, and other disorders using enantiopure deuterium-enriched bupropion. A preferred aspect of the invention provides methods of treating obesity and sexual dysfunction using enantiopure deuterium-enriched bupropion.

9 Claims, 3 Drawing Sheets

METHODS OF TREATING NEUROLOGICAL AND OTHER DISORDERS USING ENANTIOPURE DEUTERIUM-ENRICHED BUPROPION

CROSS-REFERENCE TO RELATED APPLICATIONS

This application is the national stage of International (PCT) Patent Application Serial No. PCT/US2014/071519, filed Dec. 19, 2014 which claims the benefit of and priority to U.S. Provisional Patent Application Ser. No. 61/919,155, filed Dec. 20, 2013, the contents of each of which are hereby incorporated by reference in their entirety.

FIELD OF THE INVENTION

The invention provides enantiopure deuterium-enriched bupropion, pharmaceutical compositions, and methods of treating neurological disorders, movement disorders, cardiovascular disorders, metabolic disorders, and other disorders using enantiopure deuterium-enriched bupropion.

BACKGROUND

Multiple medical disorders are linked to dysfunction of one or more neurotransmitter (e.g., dopamine, norepinephrine, and acetylcholine) systems. One class of such medical disorders is neurological disorders, such as Parkinson's disease, attention deficit hyperactivity disorder, restless legs syndrome, and sexual dysfunction, where dysfunction of the dopamine and/or norepinephrine systems have been shown to play a significant role. Dysfunction of the dopamine system has also been linked to drug addiction. Drugs such as cocaine and amphetamine have been reported to amplify the effects of dopamine. The dopamine system also has an impact on patients' cognitive function. Too little dopamine or too much dopamine has been reported to impair cognitive function, such as working memory and attention.

Therapeutics have been commercialized for treating disorders associated with dysfunction of neurotransmitter systems. One such example is bupropion hydrochloride, which has been approved by the United States Food and Drug Administration for treatment of depression, seasonal affective disorder, and as an aid for smoking cessation. Bupropion hydrochloride is marketed under the registered trademark WELLBUTRIN® and Zyban® and the prescribing information for WELLBUTRIN® explains that bupropion is an inhibitor of neuronal uptake of norepinephrine and dopamine. It is also reported that bupropion is a functional antagonist of nicotinic acetylcholine receptor subtypes such as α3, α4β3, α3β4, and α1 and that inhibition at these receptors may affect bupropion pharmacological activity. The commercialized form of bupropion hydrochloride is a racemic mixture and multiple dose-dependent adverse side effects have been reported in patients receiving this therapeutic. Exemplary side effects include, for example, seizures, agitation, dry mouth, insomnia, headache, migraine, nausea, vomiting, constipation, and tremor.

Due to the increasing number of patients suffering from neurological and other disorders associated with dysfunction of neurotransmitter systems, and the limitations of existing therapies, such as adverse side effects, there is a need for new therapeutic agents for treating medical disorders associated with such dysfunction. Attention deficit hyperactivity disorder, for example, has been reported to be one of the most common childhood disorders, and reports indicate that the number of children being diagnosed with attention deficit hyperactivity disorder is increasing. Seasonal affective disorder is another neurological disorder in need of improved therapy. Seasonal affective disorder often causes patients to experience feelings of hopelessness, increased appetite leading to weight gain, loss of energy, inability to concentrate, loss of interest in work or other activities, sluggish movements, social withdrawal, unhappiness, and/or irritability. The present invention addresses these needs and provides other related advantages.

SUMMARY OF THE INVENTION

The invention provides enantiopure deuterium-enriched bupropion, pharmaceutical compositions, and methods of treating neurological disorders, movement disorders, cardiovascular disorders, metabolic disorders, and other medical disorders using the enantiopure deuterium-enriched bupropion. The deuterated bupropion contains deuterium enrichment at the chiral center of bupropion and optionally in other locations in the compound. Further, the deuterium-enriched bupropion is provided in enantiomerically pure form. This enantiomerically pure, deuterium-enriched bupropion provides for a better therapeutic agent than non-deuterated bupropion and/or racemic mixtures of deuterium-enriched bupropion.

Accordingly, one aspect of the invention provides a deuterium-enriched compound of Formula I for use in the therapeutic methods and pharmaceutical compositions described herein. Desirably, the deuterium-enriched compound of Formula I has an optical purity of at least 75% enantiomeric excess. Formula I is represented by:

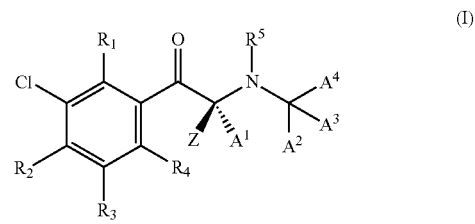

or a pharmaceutically acceptable salt thereof, wherein:
$A^1$, $A^2$, $A^3$, and $A^4$ are independently —$C(R_6)(R_7)(R_8)$;
$R_1$, $R_2$, $R_3$, $R_4$, and $R_5$ are independently H or D;
$R_6$, $R_7$, and $R_8$ each represent independently for each occurrence H or D; and
Z is H or D, provided that the abundance of deuterium in Z is at least 30%.

In certain embodiments, the deuterium-enriched compound used in the therapeutic methods and pharmaceutical compositions has the following structure:

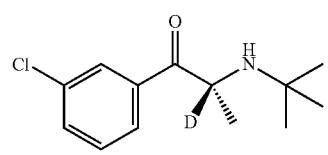 [SMILES: [2H][C@](C)(NC(C)(C)C)C(=O)c1cccc(Cl)c1]

or is a pharmaceutically acceptable salt thereof, each having an optical purity of at least 90% enantiomeric excess.

Another aspect of the invention provides a deuterium-enriched compound of Formula II for use in the therapeutic methods and pharmaceutical compositions described herein. Desirably, the deuterium-enriched compound of Formula II has an optical purity of at least 75% enantiomeric excess. Formula II is represented by:

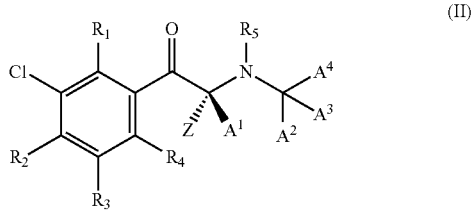

or a pharmaceutically acceptable salt thereof, wherein:
$A^1$, $A^2$, $A^3$, and $A^4$ are independently —$C(R_6)(R_7)(R_8)$;
$R_1$, $R_2$, $R_3$, $R_4$, and $R_5$ are independently H or D;
$R_6$, $R_7$, and $R_8$ each represent independently for each occurrence H or D; and
Z is H or D, provided that the abundance of deuterium in Z is at least 30%.

In certain embodiments, the deuterium-enriched compound used in the therapeutic methods and pharmaceutical compositions has the following structure:

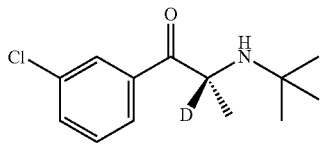 [SMILES: [2H][C@](C)(NC(C)(C)C)C(=O)c1cccc(Cl)c1]

or is a pharmaceutically acceptable salt thereof, each having an optical purity of at least 90% enantiomeric excess.

The deuterium-enriched compounds are particularly useful in the treatment of medical disorders. Exemplary medical disorders include, for example, neurological disorders, movement disorders, cardiovascular disorders, and metabolic disorders. The compounds are typically administered to a patient in the form of a pharmaceutical composition. Particularly preferred medical disorders include, for example, obesity, sexual dysfunction, neuropathic pain, attention deficit disorder, attention deficit hyperactivity disorder, and Parkinson's disease. Additional preferred medical disorders include, for example, (i) seasonal affective disorder and (ii) depression in a patient suffering from Parkinson's disease.

Accordingly, one aspect of the invention provides a method of treating a disorder selected from the group consisting of obesity, sexual dysfunction, neuropathic pain, attention deficit disorder, attention deficit hyperactivity disorder, and Parkinson's disease. The method comprises administering to a patient in need thereof a therapeutically effective amount of a deuterium-enriched compound described herein, such as a compound of Formula I or Formula II, having an optical purity of at least 75% enantiomeric excess to treat the disorder. In certain embodiments, the deuterium-enriched compound is a compound of Formula I. In certain other embodiments, the deuterium-enriched compound is a compound of Formula II.

Another aspect of the invention provides a method of treating a disorder selected from the group consisting of (i) seasonal affective disorder, (ii) depression in a patient suffering from Parkinson's disease, and (iii) treatment-resistant depression. The method comprises administering to a patient in need thereof a therapeutically effective amount of a deuterium-enriched compound described herein, such as a compound of Formula I or Formula II, having an optical purity of at least 75% enantiomeric excess to treat the disorder. In certain embodiments, the deuterium-enriched compound is a compound of Formula I. In certain other embodiments, the deuterium-enriched compound is a compound of Formula II.

Another aspect of the invention provides a method of treating a neurological disorder selected from the group consisting of Alzheimer's disease, tardive dyskinesia, Tourette syndrome, Huntington's disease, Rett syndrome, Prader-Willi syndrome, restless leg syndrome, narcolepsy, ataxia, corticobasal ganglionic degeneration dyskinesia, dystonia, tremors, multiple system atrophy, progressive supranuclear palsy, olivopontocerebellar atrophy, diffuse Lewy body disease, stiff man syndrome, apathy, generalized anxiety, panic disorder, addiction, bipolar disorder, social anxiety disorder, obsessive compulsive disorder, post-traumatic stress disorder, a sleep disorder, an eating disorder, a neuropathic condition, diabetic neuropathy, a cognitive disorder, a psychotic disorder, psychosexual dysfunction, prostate hypertrophy, migraine, bipolar depression, depression in a patient suffering from Alzheimer's disease, depression in a patient suffering from dementia, and depression in a patient suffering from hypothyroidism. The method comprises administering to a patient in need thereof a therapeutically effective amount of a deuterium-enriched compound described herein, such as a compound of Formula I or Formula II, having an optical purity of at least 75% enantiomeric excess to treat the disorder. In certain embodiments, the deuterium-enriched compound is a compound of Formula I. In certain other embodiments, the deuterium-enriched compound is a compound of Formula II.

Another aspect of the invention provides a method of treating a movement disorder selected from the group consisting of hereditary spastic paraplegia, myoclonus, spasticity, chorea, athetosis, ballism, stereotypy, tardive dystonia, tics, hemiballismus, hemi-facial spasm, psychomotor retardation, painful legs moving toes syndrome, a gait disorder, and a drug-induced movement disorder. The method comprises administering to a patient in need thereof a therapeutically effective amount of a deuterium-enriched compound described herein, such as a compound of Formula I or Formula II, having an optical purity of at least 75% enantiomeric excess to treat the disorder. In certain embodiments, the deuterium-enriched compound is a compound of Formula I. In certain other embodiments, the deuterium-enriched compound is a compound of Formula II.

Another aspect of the invention provides a method of treating a disorder selected from the group consisting of inflammatory bowel disease, psoriasis, hypotension, presyncope, syncope, Wilson's disease, shift work sleep disorder, akinetic mutism, chronic fatigue syndrome, fibromyalgia, premenstrual syndrome, premenstrual dysphoric disorder, pain, a viral infection, a cardiovascular disease, hepatic steatosis, diabetes, insulin resistance, sleep apnea, arthritis, vascular dementia, gout, calculi, and a disorder requiring a stimulant effect. The method comprises administering to a patient in need thereof a therapeutically effective amount of a deuterium-enriched compound described herein, such as a compound of Formula I or Formula II, having an optical purity of at least 75% enantiomeric excess to treat the disorder. In certain embodiments, the deuterium-enriched compound is a compound of Formula I. In certain other embodiments, the deuterium-enriched compound is a compound of Formula II.

Another aspect of the invention provides a method of reducing substance dependence by a patient selected from the group consisting of dependence on an opioid, an amphetamine, a tropane alkaloid, a hypnotic, a depressant, a hallucinogen, and combinations thereof. The method comprises administering to a patient in need thereof a therapeutically effective amount of a deuterium-enriched compound described herein, such as a compound of Formula I or Formula II, having an optical purity of at least 75% enantiomeric excess to reduce said substance dependence.

DETAILED DESCRIPTION

Figure 1:
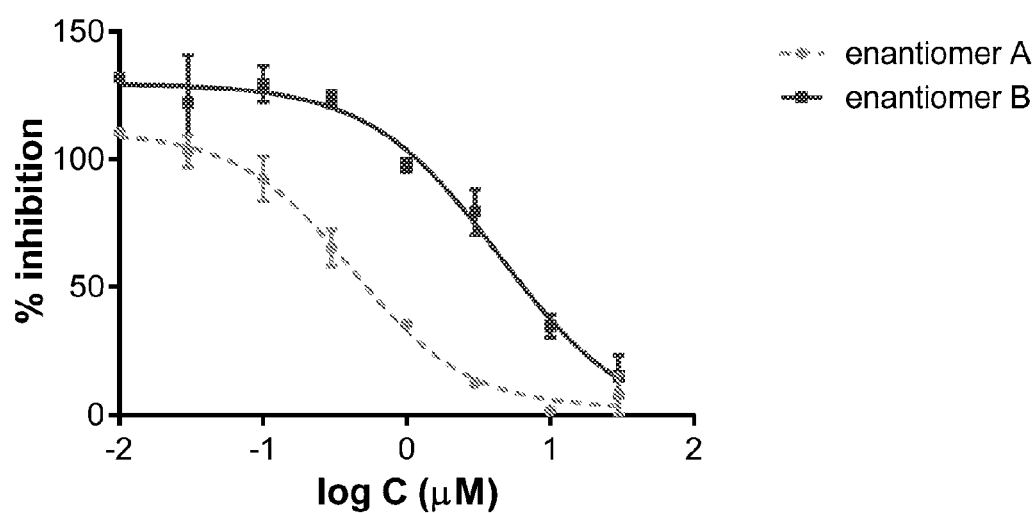
FIG. 1 is line graph and table of results from an assay measuring inhibition of dopamine uptake in rat striatum synaptosomes by enantiomers A and B, as defined in Example 2; analysis in GraphPad Prism 6 (log(inhibitor) vs. response—variable slope model); $IC_{50}$ reported in μM; as further described in Example 4 where the abbreviation "Log C" refers to the logarithm of the concentration of the stated enantiomer.

The invention provides enantiopure deuterium-enriched bupropion, pharmaceutical compositions, and methods of treating neurological disorders, movement disorders, cardiovascular disorders, metabolic disorders, and other medical disorders using enantiopure deuterium-enriched bupropion. Deuterium-enriched refers to the feature that the compound has a quantity of deuterium that is greater than in naturally occurring compounds or synthetic compounds prepared from substrates having the naturally occurring distribution of isotopes. The threshold amount of deuterium enrichment is specified in certain instances in this disclosure, and all percentages given for the amount of deuterium present are mole percentages.

Deuterium ($^2H$) is a stable, non-radioactive isotope of $^1H$ hydrogen and has an atomic weight of 2.014. Hydrogen naturally occurs as a mixture of the isotopes $^1H$ hydrogen (i.e., protium), deuterium ($^2H$), and tritium ($^3H$). The natural abundance of deuterium is 0.015%. One of ordinary skill in the art recognizes that in all chemical compounds with an H atom, the H atom actually represents a mixture of $^1H$ hydrogen, deuterium ($^2H$), and tritium ($^3H$), where about 0.015% is deuterium. Thus, compounds with a level of deuterium that has been enriched to be greater than its natural abundance of 0.015% are considered unnatural and, as a result, novel over their non-enriched counterparts.

The deuterium-enriched bupropion described herein contains deuterium enrichment at the chiral center of bupropion and optionally in other locations in the compound. Deuterium-enrichment at the chiral center reduces the rate at which the two enantiomers of bupropion may interconvert. Further, the deuterium-enriched bupropion described herein is provided in enantiomerically pure form. This enantiomerically pure, deuterium-enriched bupropion provides for a better therapeutic agent than non-deuterated bupropion and/or racemic mixtures of the compound.

Exemplary compositions and methods of the present invention are described in more detail in the following sections: I. Deuterium-enriched Bupropion; II. Therapeutic Applications; III. Dosing Considerations and Combination Therapy; and IV. Pharmaceutical Compositions. Aspects of the invention described in one particular section are not to be limited to any particular section.

I. Deuterium-Enriched Bupropion

One aspect of the invention provides deuterium-enriched compounds for use in the therapeutic methods and pharmaceutical compositions described herein. The deuterium-enriched compounds are provided in high enantiomeric purity in order to maximize therapeutic benefit, such as maximal potency per dose of therapeutic agent and minimize adverse side effects, such as seizures.

One such deuterium-enriched compound is a family of deuterium-enriched compounds represented by Formula I having an optical purity of at least 75% enantiomeric excess:

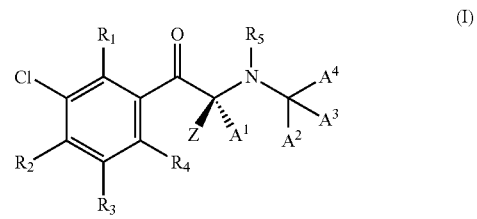

or a pharmaceutically acceptable salt thereof, wherein:
$A^1$, $A^2$, $A^3$, and $A^4$ are independently —C($R_6$)($R_7$)($R_8$);
$R_1$, $R_2$, $R_3$, $R_4$, and $R_5$ are independently H or D;
$R_6$, $R_7$, and $R_8$ each represent independently for each occurrence H or D; and
Z is H or D, provided that the abundance of deuterium in Z is at least 30%.

In certain embodiments, $A^1$ is —$CH_3$. In certain embodiments, $A^2$ is —$CH_3$. In certain embodiments, $A^3$ is —$CH_3$.

In certain embodiments, $A^4$ is —$CH_3$. In certain other embodiments, $A^1$, $A^2$, $A^3$, and $A^4$ are —$CH_3$.

In certain embodiments, $R_1$ is H. In certain embodiments, $R_2$ is H. In certain embodiments, $R_3$ is H. In certain embodiments, $R_4$ is H. In certain embodiments, $R_5$ is H. In certain other embodiments, $R_1$, $R_2$, $R_3$, $R_4$, and $R_5$ are H.

The description above describes multiple embodiments relating to compounds of Formula I. The patent application specifically contemplates all combinations of the embodiments. For example, the invention contemplates a compound of Formula I wherein $R_1$, $R_2$, $R_3$, $R_4$, and $R_5$ are H; and $A^1$ is —$CH_3$.

Another such deuterium-enriched compound is a family of deuterium-enriched compounds represented by Formula I-A having an optical purity of at least 75% enantiomeric excess:

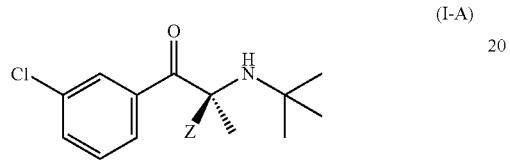

(I-A)

or a pharmaceutically acceptable salt thereof, wherein Z is H or D, provided that the abundance of deuterium in Z is at least 30%.

The compounds of Formula I and Formula I-A can be further characterized according to the abundance of deuterium at the position defined by variable Z. In certain embodiments, the abundance of deuterium in Z is selected from: (a) at least 40%, (b) at least 50%, (c) at least 60%, (d) at least 70%, (e) at least 75%, (f) at least 80%, (g) at least 90%, (h) at least 95%, (h) at least 97%, and (i) about 100%. Additional examples of the abundance of deuterium in Z include 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to about 100%.

In certain embodiments, the abundance of deuterium in Z is at least 60%. In certain other embodiments, the abundance of deuterium in Z is at least 75%. In yet other embodiments, the abundance of deuterium in Z is at least 90%.

The compounds of Formula I and Formula I-A can be further characterized according to their enantiomeric purity. In certain embodiments, the deuterium-enriched compound has an enantiomeric excess of at least 80%, 85%, 90%, 95%, or 98%. Still further examples of the optical purity include an enantiomeric excess of at least 71, 72, 73, 74, 75, 76, 77, 78, 79, 80, 81, 82, 83, 84, 85, 86, 87, 88, 89, 90, 91, 92, 93, 94, 95, 96, 97, 98, or 99%.

Still further such deuterium-enriched compounds are provided in Tables 1 and 2 below.

TABLE 1

| Compound No. | Structure |
|---|---|
| 1 | [structure: 3-Cl-phenyl-C(=O)-C(CH_3)(D)-NH-C(CH_3)_3] or a pharmaceutically acceptable salt thereof, each having an optical purity of at least 60% enantiomeric excess. |
| 2 | [structure] having an optical purity of at least 60% enantiomeric excess. |
| 3 | [structure] or a pharmaceutically acceptable salt thereof, each having an optical purity of at least 75% enantiomeric excess. |
| 4 | [structure] having an optical purity of at least 75% enantiomeric excess. |
| 5 | [structure] or a pharmaceutically acceptable salt thereof, each having an optical purity of at least 90% enantiomeric excess. |
| 6 | [structure] having an optical purity of at least 90% enantiomeric excess. |
| 7 | [structure] or a pharmaceutically acceptable salt thereof, each having an optical purity of at least 95% enantiomeric excess. |

TABLE 1-continued

| Compound No. | Structure |
|---|---|
| 8 | 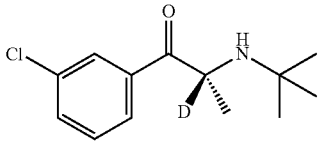 [SMILES: [2H][C@](C)(NC(C)(C)C)C(=O)c1cccc(Cl)c1] having an optical purity of at least 95% enantiomeric excess. |

TABLE 2

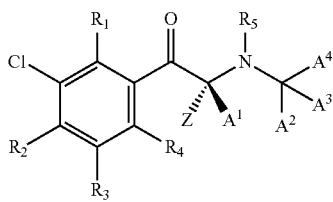

| Compound No. | Variable Definition |
|---|---|
| 1 | Z = D; $R^1$, $R^2$, $R^3$, $R^4$, and $R^5$ are H; $A^1$, $A^2$, $A^3$, and $A^4$ are —$CH_3$ |
| 2 | Z = D; $R^1$ = D; $R^2$, $R^3$, $R^4$, and $R^5$ are H; $A^1$, $A^2$, $A^3$, and $A^4$ are —$CH_3$ |
| 3 | Z = D; $R^1$ and $R^2$ = D; $R^3$, $R^4$, and $R^5$ are H; $A^1$, $A^2$, $A^3$, and $A^4$ are —$CH_3$ |
| 4 | Z = D; $R^1$, $R^2$, $R^3$, $R^4$, and $R^5$ are H; $A^1$ is $CD_3$; $A^2$, $A^3$ and $A^4$ are —$CH_3$ |
| 5 | Z = D; $R^1$, $R^2$, $R^3$, $R^4$, and $R^5$ are H; $A^1$ and $A^2$ are —$CH_3$; $A^3$ is —$CD_3$; and $A^4$ is —$CH_3$ |
| 6 | Z = D; $R^1$ and $R^2$ = D; $R^3$, $R^4$ and $R^5$ are H; $A^1$ and $A^2$ are $CD_3$; $A^3$ and $A^4$ are —$CH_3$ |

Another embodiment of the invention provides a compound in Table 2 wherein the compound has an enantiomeric excess of at least 60%, 70%, 75%, 80%, 85%, 90%, 95%, or 98%.

Another such deuterium-enriched compound is a family of deuterium-enriched compounds represented by Formula II having an optical purity of at least 75% enantiomeric excess:

(II)

or a pharmaceutically acceptable salt thereof, wherein:
$A^1$, $A^2$, $A^3$, and $A^4$ are independently —$C(R_6)(R_7)(R_8)$;
$R_1$, $R_2$, $R_3$, $R_4$, and $R_5$ are independently H or D;
$R_6$, $R_7$, and $R_8$ each represent independently for each occurrence H or D; and
Z is H or D, provided that the abundance of deuterium in Z is at least 30%.

In certain embodiments, $A^1$ is —$CH_3$. In certain embodiments, $A^2$ is —$CH_3$. In certain embodiments, $A^3$ is —$CH_3$. In certain embodiments, $A^4$ is —$CH_3$. In certain other embodiments, $A^1$, $A^2$, $A^3$, and $A^4$ are —$CH_3$.

In certain embodiments, $R_1$ is H. In certain embodiments, $R_2$ is H. In certain embodiments, $R_3$ is H. In certain embodiments, $R_4$ is H. In certain embodiments, $R_5$ is H. In certain other embodiments, $R_1$, $R_2$, $R_3$, $R_4$, and $R_5$ are H.

The description above describes multiple embodiments relating to compounds of Formula II. The patent application specifically contemplates all combinations of the embodiments. For example, the invention contemplates a compound of Formula II wherein $R_1$, $R_2$, $R_3$, $R_4$, and $R_5$ are H; and $A^1$ is —$CH_3$.

Another such deuterium-enriched compound is a family of deuterium-enriched compounds represented by Formula II-A having an optical purity of at least 75% enantiomeric excess:

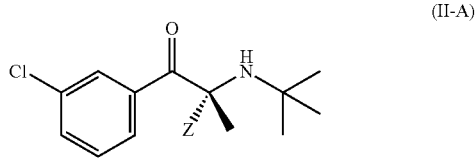

(II-A)

or a pharmaceutically acceptable salt thereof, wherein Z is H or D, provided that the abundance of deuterium in Z is at least 30%.

The compounds of Formula II and Formula II-A can be further characterized according to the abundance of deuterium at the position defined by variable Z. In certain embodiments, the abundance of deuterium in Z is selected from: (a) at least 40%, (b) at least 50%, (c) at least 60%, (d) at least 70%, (e) at least 75%, (f) at least 80%, (g) at least 90%, (h) at least 95%, (h) at least 97%, and (i) about 100%. Additional examples of the abundance of deuterium in Z include 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 to about 100%.

In certain embodiments, the abundance of deuterium in Z is at least 60%. In certain other embodiments, the abundance of deuterium in Z is at least 75%. In yet other embodiments, the abundance of deuterium in Z is at least 90%.

The compounds of Formula II and Formula II-A can be further characterized according their enantiomeric purity. In certain embodiments, the deuterium-enriched compound has an enantiomeric excess of at least 80%, 85%, 90%, 95%, or 98%. Still further examples of the optical purity include an enantiomeric excess of at least 71, 72, 73, 74, 75, 76, 77, 78, 79, 80, 81, 82, 83, 84, 85, 86, 87, 88, 89, 90, 91, 92, 93, 94, 95, 96, 97, 98, or 99%.

Still further such deuterium-enriched compounds are provided in Tables 3 and 4 below.

TABLE 3

| Compound No. | Structure |
| --- | --- |
| 1 | [structure image] <br> or a pharmaceutically acceptable salt thereof, each having an optical purity of at least 60% enantiomeric excess. |
| 2 | [structure image] <br> having an optical purity of at least 60% enantiomeric excess. |
| 3 | [structure image] <br> or a pharmaceutically acceptable salt thereof, each having an optical purity of at least 75% enantiomeric excess. |
| 4 | [structure image] <br> having an optical purity of at least 75% enantiomeric excess. |
| 5 | [structure image] <br> or a pharmaceutically acceptable salt thereof, each having an optical purity of at least 90% enantiomeric excess. |
| 6 | [structure image] <br> having an optical purity of at least 90% enantiomeric excess. |
| 7 | [structure image] <br> or a pharmaceutically acceptable salt thereof, each having an optical purity of at least 95% enantiomeric excess. |
| 8 | [structure image] <br> having an optical purity of at least 95% enantiomeric excess. |

TABLE 4

[structure image showing chlorophenyl ketone with substituents $R_1$, $R_2$, $R_3$, $R_4$, $R_5$, $Z$, $A^1$, $A^2$, $A^3$, $A^4$]

| Compound No. | Variable Definition |
| --- | --- |
| 1 | Z = D; $R^1$, $R^2$, $R^3$, $R^4$, and $R^5$ are H; $A^1$, $A^2$, $A^3$, and $A^4$ are —$CH_3$ |
| 2 | Z = D; $R^1$ = D; $R^2$, $R^3$, $R^4$, and $R^5$ are H; $A^1$, $A^2$, $A^3$, and $A^4$ are —$CH_3$ |
| 3 | Z = D; $R^1$ and $R^2$ = D; $R^3$, $R^4$, and $R^5$ are H; $A^1$, $A^2$, $A^3$, and $A^4$ are —$CH_3$ |
| 4 | Z = D; $R^1$, $R^2$, $R^3$, $R^4$, and $R^5$ are H; $A^1$ is $CD_3$; $A^2$, $A^3$ and $A^4$ are —$CH_3$ |
| 5 | Z = D; $R^1$, $R^2$, $R^3$, $R^4$, and $R^5$ are H; $A^1$ and $A^2$ are —$CH_3$; $A^3$ is —$CD_3$; and $A^4$ is —$CH_3$ |
| 6 | Z = D; $R^1$ and $R^2$ = D; $R^3$, $R^4$ and $R^5$ are H; $A^1$ and $A^2$ are $CD_3$; $A^3$ and $A^4$ are —$CH_3$ |

Another embodiment of the invention provides a compound in Table 4 wherein the compound has an enantiomeric excess of at least 60%, 70%, 75%, 80%, 85%, 90%, 95%, or 98%.

It is understood that the deuterium-enriched compounds described herein can be combined with a pharmaceutically acceptable carrier to form a pharmaceutical composition.

Deuterium-enriched compounds of the invention can generally be prepared by substituting a deuterium-enriched reagent for a non-isotopically labeled reagent in synthetic schemes reported in the literature for making non-isotopically labeled bupropion. Scheme 1 below illustrates a general method for preparing deuterium enriched bupropion. The scheme is provided for the purpose of illustrating the invention, and should not be regarded in any manner as limiting the scope or the spirit of the invention. In Scheme 1, deuterated ethyl magnesium bromide is reacted with 3-chlorobenzonitrile (A) to provide to provide 1-(3-chlorophenyl) propan-1-one (B). Then, ketone B is reacted with bromine to provide α-bromo-ketone C. Subsequent reaction of α-bromo-ketone C with tert-butyl amine provides amine D. Reaction of amine D with $D_2O$ provides racemic deutero-amine E. The R-enantiomer and S-enantiomer of deutero-amine E are separated using chiral chromatography, such as chiral high-performance liquid chromatography. Alternatively, the R-enantiomer and S-enantiomer of deutero-amine E may be separated by reaction with a chiral carboxylic acid to form a salt, followed by separation of the resulting diastereomeric salts, and conversion of the separated salts back to deuterated bupropion free base in enantio-pure form.

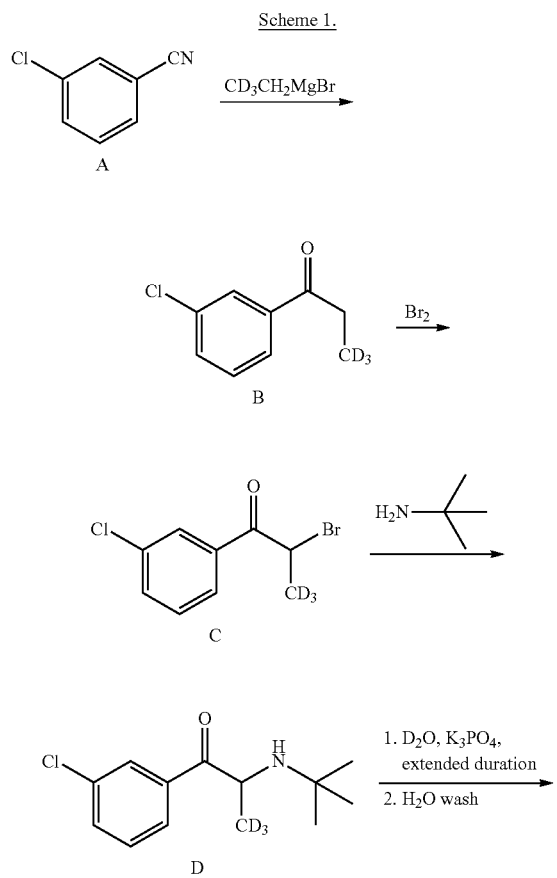

Scheme 1.

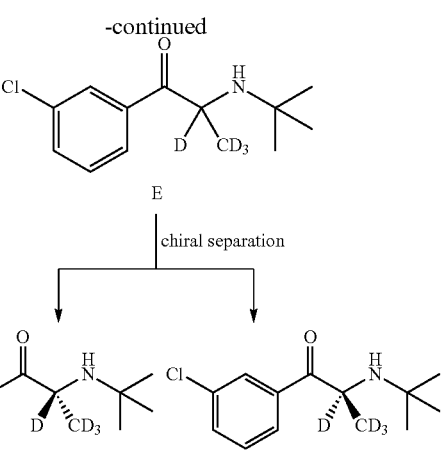

Compounds having deuterium enrichment at a position other than the methyl adjacent to the carbonyl group can be prepared using non-deuterated ethyl magnesium bromide and using a deuterated 3-chlorobenzonitrile and/or deuterated tert-butyl amine. Further, compounds can be made having deuterium enrichment at the methyl adjacent to the carbonyl group and one or both of (i) deuterium enrichment on the phenyl portion of bupropion and (ii) deuterium enrichment on one or more of the methyl groups of the tert-butyl amine portion of bupropion.

Compounds having deuterium enrichment only at the α-carbonyl position can be prepared by reacting non-isotopically enriched bupropion with $D_2O$ in a buffer for an extended duration to provide bupropion having deuterium enrichment at the α-carbonyl position. Further description of such procedures is provided in, for instance, the Examples in the present application.

Compounds described herein can be provided in isolated or purified form. Isolated or purified compounds are a group of compounds that have been separated from their environment, such as from a crude reaction mixture if made in a laboratory setting or removed from their natural environment if naturally occurring. Examples of the purity of the isolated compound include, for example, at least 50%, 55%, 60%, 65%, 70%, 75%, 80%, 85%, 90%, 95%, to 100% by weight.

Another aspect of the invention provides a unit quantum of a deuterium-enriched compound described herein, such as an amount of at least (a) one μg of a disclosed deuterium-enriched compound, (b) one mg, or (c) one gram. In further embodiments, the quantum is, for example, at least 0.01, 0.02, 0.03, 0.04, 0.05, 0.1, 0.2, 0.3, 0.4, 0.5, or 1 mole of the compound. The present amounts also cover lab-scale (e.g., gram scale including 1, 2, 3, 4, 5 g, etc.), kilo-lab scale (e.g., kilogram scale including 1, 2, 3, 4, 5 kg, etc.), and industrial or commercial scale (e.g., multi-kilogram or above scale including 100, 200, 300, 400, 500 kg, etc.) quantities as these will be more useful in the actual manufacture of a pharmaceutical. Industrial/commercial scale refers to the amount of product that would be produced in a batch that was designed for clinical testing, formulation, sale/distribution to the public, etc.

II. Therapeutic Applications

The invention provides methods of using deuterium-enriched compounds described herein to treat medical disorders. Preferred medical disorders for treatment include neurological disorders, movement disorders, metabolic disorders, and cardiovascular disorders. Use of the deuterium-enriched compounds having high enantiomeric purity is contemplated to maximize therapeutic benefit, such as achieving increased potency per dose of therapeutic agent and minimize adverse side effects. The deuterium-enriched compound can be, for example, a compound of Formula I, Formula I-A, Formula II, Formula II-A, or one of the other deuterium-enriched compounds described in Section I above.

Accordingly, one aspect of the invention provides a method of treating a disorder selected from the group consisting of obesity, sexual dysfunction, neuropathic pain, attention deficit disorder, attention deficit hyperactivity disorder, and Parkinson's disease. The method comprises administering to a patient in need thereof a therapeutically effective amount of a deuterium-enriched compound described herein, such as a compound of Formula I or Formula II, having an optical purity of at least 75% enantiomeric excess to treat the disorder. In certain embodiments, the deuterium-enriched compound is a compound of Formula I. In certain other embodiments, the deuterium-enriched compound is a compound of Formula II.

Obesity generally refers to the medical condition in which the patient suffers from excess body fat. Obesity is a leading preventable cause of death worldwide, and is considered by various authorities to be a serious public health problem. As such, in certain embodiments, the disorder to be treated is obesity.

Sexual dysfunction generally refers to difficulty experienced by an individual during any stage of normal sexual activity, including physical pleasure, desire, preference, arousal or orgasm. Sexual dysfunction can have a significant impact on an individual's perceived quality of sexual life. As such, in certain embodiments, the disorder to be treated is sexual dysfunction. The sexual dysfunction can be female sexual dysfunction, which can be characterized by one or more of the following insofar as the event causes distress: hypoactive sexual desire, sexual aversion, sexual arousal disorder, and/or orgasmic disorder. In certain other embodiments, the sexual dysfunction is female hyposexual desire disorder. In yet other embodiments, the sexual dysfunction is male sexual dysfunction, such as premature ejaculation or male hyposexual desire disorder.

Neuropathic pain generally refers to pain caused by damage or disease that affects the somatosensory system. Neuropathic pain can result from disorders of the peripheral nervous system or the central nervous system (e.g., brain and spinal cord). A substantial percentage of the population, particularly the European population suffers from neuropathic pain. As such, in certain embodiments, the disorder to be treated is neuropathic pain. The neuropathic pain can be, for example, a postherpetic neuralgia, a trigeminal neuralgia, phantom limb pain, pain associated with diabetic neuropathy, and/or pain associated with carpal tunnel syndrome.

Attention deficit hyperactivity disorder generally refers to the art-recognized condition in which a patient suffers from significant problems of attention and/or hyperactivity and acting impulsively that are not appropriate for a person's age. An increasing number of children are being diagnosed with attention deficit disorder and attention deficit hyperactivity disorder, and a significant percentage of children with attention deficit hyperactivity disorder or attention deficit disorder continue to suffer from the disorder in adulthood. As such, in certain embodiments, the disorder to be treated is attention deficit hyperactivity disorder.

In certain embodiments, the attention deficit disorder is adult attention deficit disorder.

Facilitating Weight Loss and/or Reducing Cholesterol

Another aspect of the invention provides a method of facilitating weight loss in a patient. The method comprises administering to a patient in need thereof an effective amount of a deuterium-enriched compound described herein, such as a compound of Formula I or Formula II, having an optical purity of at least 75% enantiomeric excess to facilitate weight loss. In certain embodiments, the deuterium-enriched compound is a compound of Formula I. In certain other embodiments, the deuterium-enriched compound is a compound of Formula II.

In certain embodiments, the method produces at least a 1%, 2%, or 5% reduction in bodyweight of the patient.

Another aspect of the invention provides a method of reducing the amount of cholesterol in a patient. The method comprises administering to a patient in need thereof an effective amount of a deuterium-enriched compound described herein, such as a compound of Formula I or Formula II, having an optical purity of at least 75% enantiomeric excess to reduce the amount of cholesterol in the patient. In certain embodiments, the deuterium-enriched compound is a compound of Formula I. In certain other embodiments, the deuterium-enriched compound is a compound of Formula II.

In certain embodiments, the method produces at least a 1%, 2%, or 5% reduction in the amount of cholesterol in the patient.

Treating Seasonal Affective Disorder, Depression in Parkinson's Disease Patients, and Treatment-Resistant Depression Another aspect of the invention provides a method of treating a disorder selected from the group consisting of (i) seasonal affective disorder, (ii) depression in a patient suffering from Parkinson's disease, and (iii) treatment-resistant depression. The method comprises administering to a patient in need thereof a therapeutically effective amount of a deuterium-enriched compound described herein, such as a compound of Formula I or Formula II, having an optical purity of at least 75% enantiomeric excess to treat the disorder. In certain embodiments, the deuterium-enriched compound is a compound of Formula I. In certain other embodiments, the deuterium-enriched compound is a compound of Formula II.

Seasonal affective disorder generally refers to the recurrent major depressive disorder that coincides with the seasonal pattern that occurs at a specific time of the year and fully remits otherwise. Patients suffering from seasonal affective disorder may experience difficulty waking up in the morning, morning sickness, tendency to oversleep and overeat, and cravings for carbohydrates. This disorder is sometimes more prevalent in winter months, particularly in geographies that experience reduced daylight hours. Winter seasonal affective disorder is characterized by the onset of depression in the fall or winter followed by recovery in the spring. As such, in certain embodiments, the disorder to be treated is seasonal affective disorder.

Depression in patients suffering from Parkinson's disease is a frequent complication. The Parkinson's Disease Foundation has reported that up to sixty percent of patients suffering from Parkinson's disease exhibit mild to moderate depression. As such, in certain embodiments, the disorder to be treated is depression in a patient suffering from Parkinson's disease.

Treating Neurological Disorders

Another aspect of the invention provides a method of treating a neurological disorder selected from the group consisting of Alzheimer's disease, tardive dyskinesia, Tourette syndrome, Huntington's disease, Rett syndrome, Prader-Willi syndrome, restless leg syndrome, narcolepsy, ataxia, corticobasal ganglionic degeneration dyskinesia, dystonia, tremors, multiple system atrophy, progressive supranuclear palsy, olivopontocerebellar atrophy, diffuse Lewy body disease, stiff man syndrome, apathy, generalized anxiety, panic disorder, addiction, bipolar disorder, social anxiety disorder, obsessive compulsive disorder, post-traumatic stress disorder, a sleep disorder, an eating disorder, a neuropathic condition, diabetic neuropathy, a cognitive disorder, a psychotic disorder, psychosexual dysfunction, prostate hypertrophy, migraine, bipolar depression, depression in a patient suffering from Alzheimer's disease, depression in a patient suffering from dementia, and depression in a patient suffering from hypothyroidism. The method comprises administering to a patient in need thereof a therapeutically effective amount of a deuterium-enriched compound described herein, such as a compound of Formula I or Formula II, having an optical purity of at least 75% enantiomeric excess to treat the disorder. In certain embodiments, the deuterium-enriched compound is a compound of Formula I. In certain other embodiments, the deuterium-enriched compound is a compound of Formula II.

In certain embodiments, the neurological disorder is a sleep disorder, such as hypersomnia and/or sleep apnea.

In certain embodiments, the neurological disorder is a cognitive disorder, such as cognitive impairment and/or memory impairment. The cognitive impairment may be, for example, cognitive impairment associated with ADHD, Alzheimer's disease, Prader-Willi syndrome, senile dementia, traumatic brain injury, and/or pathogenic brain injury. In certain other embodiments, the neurological disorder is an eating disorder, such as bulimia.

In certain embodiments, the neurological disorder is addiction, such as gambling addiction, sex addiction, or drug addiction, such as addiction to one or more of a stimulant, cocaine, tobacco, an opioid, nicotine, alcohol, an amphetamine, or a psychostimulant. In certain embodiments, the drug addiction is methamphetamine dependence. In yet other embodiments, the drug addiction is an addiction to one or more of an opioid, a stimulant, a hypnotic, a depressant, or a hallucinogen.

Another aspect of the invention provides a method of improving cognition in a patient suffering from a neurological disorder, such as Alzheimer's disease, Parkinson's disease, attention deficit hyperactivity disorder, dementia (such as senile dementia), or one of the other neurological disorders described herein. The method comprises administering to a patient in need thereof a therapeutically effective amount of a deuterium-enriched compound described herein, such as a compound of Formula I or Formula II, having an optical purity of at least 75% enantiomeric excess to improve cognition.

Another aspect of the invention provides a method of reducing a withdrawal symptom associated with reduced consumption of an illicit drug by a patient. The method comprises administering to a patient in need thereof a therapeutically effective amount of a deuterium-enriched compound described herein, such as a compound of Formula I or Formula II, having an optical purity of at least 75% enantiomeric excess to reduce the frequency or intensity of a withdrawal symptom associated with reduced consumption of an illicit drug by a patient. The withdrawal symptom may be, for example, anxiety, restlessness, irritability, insomnia, headache, poor concentration, depression, social isolation, sweating, racing heart, palpitations, muscle tension, tightness in the chest, difficulty breathing, tremor, nausea, vomiting, diarrhea, hallucination, stroke, heart attack, and/or grand mal seizure. The illicit drug may be an opioid, a stimulant, a hypnotic, a depressant, or a hallucinogen. In yet other embodiments, the illicit drug may be an opioid (e.g., heroin), an amphetamine stimulant (e.g., methamphetamine or mephedrone), a tropane alkaloid (e.g., cocaine), a hypnotic, a depressant, or a hallucinogen. In certain embodiments, the deuterium-enriched compound is a compound of Formula I. In certain other embodiments, the deuterium-enriched compound is a compound of Formula II.

Another aspect of the invention provides a method of reducing a rewarding effect of an illicit drug upon consumption of the illicit drug by the patient. The method comprises administering to a patient in need thereof a therapeutically effective amount of a deuterium-enriched compound described herein, such as a compound of Formula I or Formula II, having an optical purity of at least 75% enantiomeric excess to reduce the reward effect produced by an illicit drug upon consumption of the illicit drug by the patient. The rewarding effect may be, for example, euphoria and/or increased energy. The illicit drug may be an opioid, a stimulant, a hypnotic, a depressant, or a hallucinogen. In yet other embodiments, the illicit drug may be an opioid (e.g., heroin), an amphetamine stimulant (e.g., methamphetamine or mephedrone), a tropane alkaloid (e.g., cocaine), a hypnotic, a depressant, or a hallucinogen.

Another aspect of the invention provides a method for treating the effects of ethanol in a patient. The method comprises administering to a patient in need thereof a therapeutically effective amount of a deuterium-enriched compound described herein, such as a compound of Formula I or Formula II, having an optical purity of at least 75% enantiomeric excess to treat the effects of ethanol. In certain embodiments, the deuterium-enriched compound is a compound of Formula I. In certain other embodiments, the deuterium-enriched compound is a compound of Formula II.

Treating Movement Disorders

Another aspect of the invention provides a method of treating a movement disorder selected from the group consisting of hereditary spastic paraplegia, myoclonus, spasticity, chorea, athetosis, ballism, stereotypy, tardive dystonia, tics, hemiballismus, hemifacial spasm, psychomotor retardation, painful legs moving toes syndrome, a gait disorder, and a drug-induced movement disorder. The method comprises administering to a patient in need thereof a therapeutically effective amount of a deuterium-enriched compound described herein, such as a compound of Formula I or Formula II, having an optical purity of at least 75% enantiomeric excess to treat the disorder. In certain embodiments, the deuterium-enriched compound is a compound of Formula I. In certain other embodiments, the deuterium-enriched compound is a compound of Formula II.

In certain embodiments, the chorea is Sydenham's chorea.

Treating Additional Medical Disorders

Another aspect of the invention provides a method of treating a disorder selected from the group consisting of inflammatory bowel disease, psoriasis, hypotension, presyncope, syncope, Wilson's disease, shift work sleep disorder, akinetic mutism, chronic fatigue syndrome, fibromyalgia, premenstrual syndrome, premenstrual dysphoric disorder, pain, a viral infection, a cardiovascular disease (e.g., hypertension, heart failure, dyslipidemia, hypercholesterolemia, hypertriglyceridemia, or hyperlipoproteinemia), hepatic steatosis, diabetes, insulin resistance, sleep apnea, arthritis, vascular dementia, gout, calculi, and a disorder requiring a stimulant effect. The method comprises administering to a patient in need thereof a therapeutically effective amount of a deuterium-enriched compound described herein, such as a compound of Formula I or Formula II, having an optical purity of at least 75% enantiomeric excess to treat the disorder. In certain embodiments, the deuterium-enriched compound is a compound of Formula I. In certain other embodiments, the deuterium-enriched compound is a compound of Formula II.

In certain embodiments, the disorder is pain, such as chronic pain, pain associated with depression, persistent headache, or reflex sympathetic dystrophy. In certain embodiments, the disorder is a cardiovascular disease, such as hypertension, heart failure, dyslipidemia, hypercholesterolemia, hypertriglyceridemia, or hyperlipoproteinemia.

Reducing Substance Dependence

Another aspect of the invention provides a method of reducing dependence by a patient to a substance selected from the group consisting of an opioid, an amphetamine, a tropane alkaloid, a hypnotic, an anti-depressant, a hallucinogen, a pain medication, a sleep medication, and combinations thereof. The method comprises administering to a patient in need thereof a therapeutically effective amount of a deuterium-enriched compound described herein, such as a compound of Formula I or Formula II, having an optical purity of at least 75% enantiomeric excess to reduce said substance dependence. The reduction in dependence may be at least a 10%, 25%, 50%, 75% or 95% reduction in dependence according to the standard test for measuring substance dependence used in current U.S. medical practice. In certain embodiments, the substance may be an opioid (e.g., heroin), an amphetamine (e.g., methamphetamine or mephedrone), a tropane alkaloid (e.g., cocaine), a hypnotic, an anti-depressant, or a hallucinogen. In certain embodiments, the substance is methamphetamine or cocaine.

Another aspect of the invention provides a method of reducing dependence by a patient to a benzodiazepine. The method comprises administering to a patient in need thereof a therapeutically effective amount of a deuterium-enriched compound described herein, such as a compound of Formula I or Formula II, having an optical purity of at least 75% enantiomeric excess to reduce said dependence on a benzodiazepine. The reduction in dependence may be at least a 10%, 25%, 50%, 75% or 95% reduction in dependence according to the standard test for measuring benzodiazepine dependence used in current U.S. medical practice.

Additional Features of Therapeutic Methods

The therapeutic methods can be further characterized according to blood plasma stability of the deuterated enantiomer of bupropion administered to the patient. In certain embodiments, the molar ratio of S-enantiomer to R-enantiomer of deuterated bupropion present in the patient's blood plasma measured at 30 minutes (or 1 hr, 2 hr, 3 hr, 4 hr, 5 hr, or 6 hr) after administration of the deuterated bupropion is within 10% (or 5%, 15%, 20%, 25%, 30%, 35%, 40%, 45%, or 50%) of the molar ratio of S-enantiomer to R-enantiomer of deuterated bupropion administered to the patient.

The therapeutic methods can be further characterized according to the magnitude of improvement in efficacy relative to administering an equimolar amount of non-isotopically enriched bupropion, e.g., non-isotopically enriched bupropion having the same ratio of S-enantiomer to R-enantiomer as that deuterium-enriched bupropion administered to the patient. In certain embodiments, the magnitude of improvement is at least a 10%, 20%, 30%, 40%, 50%, 60%, 70%, 80%, 90%, 100%, 125%, 150%, 175%, 200%, 250%, 300%, 350%, or 400% improvement. In certain embodiments, the magnitude of improvement is in the range of about 10% to 30%, about 30% to 50%, about 50% to 70%, about 70% to 90%, about 90% to 100%, about 100% to 125%, about 125% to 150%, about 150% to 175%, or about 175% to 200% improvement.

The therapeutic methods can be further characterized according to the magnitude of reduction in an adverse side effect (e.g., seizure) relative to administering an equimolar amount of non-isotopically enriched bupropion, e.g., non-isotopically enriched bupropion having the same ratio of S-enantiomer to R-enantiomer as that deuterium-enriched bupropion administered to the patient. In certain embodiments, the magnitude of reduction in an adverse side effect (e.g., seizure) is at least a 10%, 20%, 30%, 40%, 50%, 60%, 70%, 80%, 90%, 100%, 125%, 150%, 175%, 200%, 250%, 300%, 350%, or 400%. In certain embodiments, the magnitude of reduction in an adverse side effect is in the range of about 10% to 30%, about 30% to 50%, about 50% to 70%, about 70% to 90%, about 90% to 100%, about 100% to 125%, about 125% to 150%, about 150% to 175%, or about 175% to 200%. In certain embodiments, the side effect is seizure, hepatic impairment, cardiovascular disorder (e.g., hypertension, hypotension, or palpitations), renal impairment, dizziness, constipation, anorexia, headache, dry mouth, agitation, or blurred vision. In certain embodiments, the side effect is seizure.

The therapeutic methods can be further characterized according to the magnitude of improvement in therapeutic index relative to administering an equimolar amount of non-isotopically enriched bupropion, e.g., non-isotopically enriched bupropion having the same ratio of S-enantiomer to R-enantiomer as that deuterium-enriched bupropion administered to the patient. In certain embodiments, the magnitude of improvement is at least a 1.5, 2, 5, 10, 15, 20, 25, 30, 35, 40, 45, 50, 55, 60, 65, or 70 fold improvement. In certain embodiments, the magnitude of improvement is at least a 30, 35, 40, 45, or 50 fold improvement. In certain embodiments, the magnitude of improvement is in the range of a 2-10, 10-20, 20-30, 30-40, 40-50, or 50-60 fold improvement.

Manufacture of Medicaments

Another aspect of the invention provides for the use of a deuterium-enriched compound described herein for the manufacture of a medicament. The medicament may be for treating one or more of the medical disorders described herein, such as treating obesity, sexual dysfunction, neuropathic pain, or attention deficit hyperactivity disorder.

III. Dosing Considerations and Combination Therapy

Doses of a compound provided herein, or a pharmaceutically acceptable salt thereof, vary depending on factors such as: specific indication to be treated; age and condition of a patient; and amount of second active agent used, if any. Generally, a compound provided herein, or a pharmaceutically acceptable salt thereof, may be used in an amount of from about 0.1 mg to about 1 g per day, or from about 0.1 mg to about 500 mg per day, and can be adjusted in a conventional fashion (e.g., the same amount administered each day of the treatment), in cycles (e.g., one week on, one week off), or in an amount that increases or decreases over the course of treatment. In other embodiments, the dose can be from about 1 mg to 1000 mg, from about 1 mg to about 450 mg, from about 0.1 mg to about 150 mg, from about 1 mg to about 300 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg. In yet other embodiments, the daily dose can be from about 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, 275 mg to 300 mg, 300 mg to 325 mg, 325 mg to 350 mg, 350 mg to 375 mg, 375 mg to 400 mg, 400 mg to 425 mg, or 425 mg to 450 mg. In certain embodiments, the deuterium-enriched bupropion is administered at a daily dosage in the range of about 125 mg to 150 mg, 150 mg to 175 mg, 175 mg to 200 mg, 200 mg to 225 mg, 225 mg to 250 mg, 250 mg to 275 mg, or 275 mg to 300 mg. In certain embodiments, the deuterium-enriched bupropion is administered at a daily dosage in the range of about 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, or 275 mg to 300 mg. In certain embodiments, the deuterium-enriched bupropion is administered at a daily dosage in the range of about 125 mg to 150 mg or 150 mg to 175 mg. In certain embodiments, the deuterium-enriched bupropion is administered at a daily dosage in the range of about 125 mg to 175 mg. In certain embodiments, the deuterium-enriched bupropion is administered at a daily dosage in the range of about 140 mg to 160 mg. In yet other embodiments, the deuterium-enriched bupropion is administered at a daily dosage in the range of about 50 mg to 175 mg, or about 125 mg to 175 mg. In yet other embodiments, the daily dose is less than about 50 mg, 75 mg, 100 mg, 125 mg, 150 mg, 175 mg, 200 mg, 225 mg, 250 mg, 275 mg, 300 mg, 325 mg, 350 mg, 375 mg, 400 mg, 425 mg, or 450 mg. In yet other embodiments, the daily dose is less than about 125 mg, 150 mg, or 175 mg.

In certain aspects, the therapeutic agents provided herein are cyclically administered to a patient. Cycling therapy involves the administration of an active agent for a period of time, followed by a rest (i.e., discontinuation of the administration) for a period of time, and repeating this sequential administration. Cycling therapy can reduce the development of resistance to one or more of the therapies. These regimens can avoid or reduce the side effects of one of the therapies, and/or improve the efficacy of the treatment.

Consequently, in another aspect, a compound provided herein is administered daily in a single or divided doses in a four to six week cycle with a rest period of about a week or two weeks. Cycling therapy further allows the frequency, number, and length of dosing cycles to be increased. Thus, another aspect encompasses the administration of a compound provided herein for more cycles than are typical when it is administered alone. In yet another aspect, a compound provided herein is administered for a greater number of cycles than would typically cause dose-limiting toxicity in a patient to whom a second active ingredient is not also being administered.

In another aspect, a compound provided herein is administered daily and continuously for three or four weeks at a dose of from about 0.1 mg to about 1000 mg per day, followed by a rest of one or two weeks. In other embodiments, the dose can be from about 1 mg to about 450 mg, from about 0.1 mg to about 150 mg, from about 1 mg to about 300 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg, followed by a rest.

In another aspect, a compound provided herein and a second active ingredient are administered orally or parenterally, with administration of the compound provided herein occurring prior to (e.g., about 30 to 60 minutes) the second active ingredient, during a cycle of four to six weeks. In certain embodiments, the compound and second active agent are administered as a single dosage or they are administered separately. In another aspect, the combination of a compound provided herein and a second active ingredient is administered by intravenous infusion over about 90 minutes every cycle.

Typically, the number of cycles during which the combination treatment is administered to a patient will be from about one to about 24 cycles, from about two to about 16 cycles, or from about three to about four cycles.

Combination Therapy

A compound provided herein, or a pharmaceutically acceptable salt thereof, can be combined with other pharmacologically active compounds ("second active agents") in methods and compositions provided herein. Certain combinations may work synergistically in the treatment of particular types of diseases or disorders, and conditions and symptoms associated with such diseases or disorders. A compound provided herein, or a pharmaceutically acceptable salt thereof, can also work to alleviate adverse effects associated with certain second active agents, and vice versa.

One or more second active ingredients or agents can be used in the methods and compositions provided herein. Second active agents can be large molecules (e.g., proteins) or small molecules (e.g., synthetic inorganic, organometallic, or organic molecules).

In certain embodiments, the combination therapy comprises a deuterium-enriched compound described herein and one or more of naltrexone, liraglutide, topiramate, and phentermine. Such combination therapy can be particular useful for the treatment of obesity or metabolic syndrome.

In certain embodiments, the combination therapy comprises a deuterium-enriched compound described herein and zonisamide. In certain embodiments, the combination therapy comprises a deuterium-enriched compound described herein and naltrexone. Such combination therapies can be particular useful for the treatment of obesity.

In certain other embodiments, the combination therapy comprises a deuterium-enriched compound described herein and trazodone. Such combination therapy can be particular useful for the treatment of sexual dysfunction.

In certain other embodiments, the combination therapy comprises a deuterium-enriched compound described herein and escitalopram. Such combination therapy can be particular useful for the treatment of bipolar disorder.

Administration of a compound provided herein, or a pharmaceutically acceptable salt thereof, and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. One route of administration for compounds provided herein is oral. Routes of administration for the second active agents or ingredients are known to those of ordinary skill in the art. See, e.g., Physicians' Desk Reference (60$^{th}$ Ed., 2006).

IV. Pharmaceutical Compositions

The invention provides pharmaceutical compositions comprising a deuterium-enriched compound described herein, such as a compound of Formula I or II, and a pharmaceutically acceptable carrier. In certain embodiments, the pharmaceutical compositions comprise a therapeutically-effective amount of a deuterium-enriched compound described herein, such as a compound of Formula I or II, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets (e.g., those targeted for buccal, sublingual, and/or systemic absorption), boluses, powders, granules, pastes for application to the tongue; (2) parenteral administration by, for example, subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

Pharmaceutical compositions can be used in the preparation of individual, single unit dosage forms. Pharmaceutical compositions and dosage forms provided herein comprise a compound provided herein, or a pharmaceutically acceptable salt thereof. Pharmaceutical compositions and dosage forms can further comprise one or more excipients. Additionally, pharmaceutical compositions and dosage forms provided herein can comprise one or more additional active ingredients. Examples of optional second, or additional, active ingredients are described above.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another and will be readily apparent to those skilled in the art. See, e.g., Remington's Pharmaceutical Sciences, 18th ed., Mack Publishing, Easton Pa. (1990).

The suitability of a particular excipient may depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose other mono- or disaccharides. As used herein, the term "lactose-free" means that the amount of lactose present, if any, is insufficient to substantially increase the degradation rate of an active ingredient. Lactose-free compositions can comprise excipients that are well known in the art and are listed, for example, in the U.S. Pharmacopeia (USP) 25-NF20 (2002). In general, lactose-free compositions comprise active ingredients, a binder/filler, and a lubricant in pharmaceutically compatible and pharmaceutically acceptable amounts. In another aspect, lactose-free dosage forms comprise active ingredients, microcrystalline cellulose, pre-gelatinized starch, and magnesium stearate.

Also provided are anhydrous pharmaceutical compositions and dosage forms comprising active ingredients. Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected. An anhydrous pharmaceutical composition should be prepared and stored such that its anhydrous nature is maintained. Accordingly, anhydrous compositions are, in another aspect, packaged using materials known to prevent exposure to water such that they can be included in suitable formulary kits. Examples of suitable packaging include, but are not limited to, hermetically sealed foils, plastics, dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. In another aspect, dosage forms comprise a compound provided herein in an amount of from about 0.10 to about 500 mg. Examples of dosages include, but are not limited to, 0.1, 1, 2, 5, 7.5, 10, 12.5, 15, 17.5, 20, 25, 50, 100, 150, 200, 250, 300, 350, 400, 450, or 500 mg.

In another aspect, dosage forms comprise the second active ingredient in an amount of 1 to about 1000 mg, from about 5 to about 500 mg, from about 10 to about 350 mg, or from about 50 to about 200 mg. Of course, the specific amount of the second active agent will depend on the specific agent used, the diseases or disorders being treated or managed, and the amount(s) of a compound provided herein, and any optional additional active agents concurrently administered to the patient.

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, Remington's Pharmaceutical Sciences, 18th ed., Mack Publishing, Easton Pa. (1990).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In another aspect, the invention provides oral dosage forms that are tablets or capsules, in which case solid excipients are employed. In another aspect, the tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl-pyrrolidone, methyl cellulose, pre-gelatinized starch, hydroxypropyl methyl cellulose, (e.g., Nos. 2208, 2906, 2910), microcrystalline cellulose, and mixtures thereof.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in another aspect, present in from about 50 to about 99 weight percent of the pharmaceutical composition or dosage form.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In another aspect, pharmaceutical compositions comprise from about 0.5 to about 15 weight percent of disintegrant, or from about 1 to about 5 weight percent of disintegrant. Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laurate, agar, and mixtures thereof. Additional lubricants include, for example, a Syloid® silica gel (AEROSIL200, manufactured by W. R. Grace Co. of Baltimore, Md.), a coagulated aerosol of synthetic silica (marketed by Degussa Co. of Piano, Tex.), CAB-O-SIL (a pyrogenic silicon dioxide product sold by Cabot Co. of Boston, Mass.), and mixtures thereof. If used at all, lubricants may be used in an amount of less than about 1 weight percent of the pharmaceutical compositions or dosage forms into which they are incorporated.

In another aspect, the invention provides a solid oral dosage form comprising a compound provided herein, anhydrous lactose, microcrystalline cellulose, polyvinylpyrrolidone, stearic acid, colloidal anhydrous silica, and gelatin.

Active ingredients provided herein can also be administered by controlled release means or by delivery devices that are well known to those of ordinary skill in the art. Examples include, but are not limited to, those described in U.S. Pat. Nos. 3,845,770; 3,916,899; 3,536,809; 3,598,123; 4,008,719, 5,674,533, 5,059,595, 5,591,767, 5,120,548, 5,073,543, 5,639,476, 5,354,556, and 5,733,566, each of which is incorporated in its entirety herein by reference. Such dosage forms can be used to provide slow or controlled-release of one or more active ingredients using, for example, hydroxypropyl methyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active agents provided herein. In another aspect, the invention provides single unit dosage forms suitable for oral administration such as, but not limited to, tablets, capsules, gel caps, and caplets that are adapted for controlled-release.

Parenteral dosage forms can be administered to patients by various routes including, but not limited to, subcutaneous, intravenous (including bolus injection), intramuscular, and intraarterial. Administration of a parenteral dosage form bypasses a patient's natural defenses against contaminants, and thus, in these aspects, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions. Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of a compound provided herein. See, e.g., U.S. Pat. No. 5,134,127, which is incorporated in its entirety herein by reference.

Topical and mucosal dosage forms provided herein include, but are not limited to, sprays, aerosols, solutions, emulsions, suspensions, eye drops or other ophthalmic preparations, or other forms known to one of skill in the art. See, e.g., Remington's Pharmaceutical Sciences, 16th and 18th eds., Mack Publishing, Easton Pa. (1980 & 1990); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein are well known to those skilled in the pharmaceutical arts, and depend on the particular tissue to which a given pharmaceutical composition or dosage form will be applied. In another aspect, excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are nontoxic and pharmaceutically acceptable. Moisturizers or humectants can also be added to pharmaceutical compositions and dosage forms. Examples of additional ingredients are well known in the art. See, e.g., Remington's Pharmaceutical Sciences, 16th and 18th eds., Mack Publishing, Easton Pa. (1980 & 1990).

The pH of a pharmaceutical composition or dosage form may also be adjusted to improve delivery of one or more active ingredients. Also, the polarity of a solvent carrier, its ionic strength, or tonicity can be adjusted to improve delivery. Compounds such as stearates can also be added to pharmaceutical compositions or dosage forms to alter the hydrophilicity or lipophilicity of one or more active ingredients so as to improve delivery. In other aspects, stearates can serve as a lipid vehicle for the formulation, as an emulsifying agent or surfactant, or as a delivery-enhancing or penetration-enhancing agent. In other aspects, salts of the active ingredients can be used to further adjust the properties of the resulting composition.

In another aspect, the active ingredients provided herein are not administered to a patient at the same time or by the same route of administration. In another aspect, provided are kits which can simplify the administration of appropriate amounts of active ingredients.

In another aspect, the invention provides a kit comprising a dosage form of a compound provided herein. Kits can further comprise additional active ingredients or a pharmacologically active mutant or derivative thereof, or a combination thereof. Examples of the additional active ingredients include, but are not limited to, those disclosed herein.

In other aspects, the kits can further comprise devices that are used to administer the active ingredients. Examples of such devices include, but are not limited to, syringes, drip bags, patches, and inhalers.

V. Definitions

To facilitate an understanding of the present invention, a number of terms and phrases are defined below.

The term "compound" refers to a quantity of molecules that is sufficient to be weighed, tested for its structural identity, and to have a demonstrable use (e.g., a quantity that can be shown to be active in an assay, an in vitro test, or in vivo test, or a quantity that can be administered to a patient and provide a therapeutic benefit).

Unless indicated otherwise, when a D is specifically recited at a position or is shown in a formula, this D represents a mixture of hydrogen and deuterium where the amount of deuterium is about 100% (i.e., the abundance of deuterium ranges from greater than 90% up to 100%). In certain embodiments, the abundance of deuterium in D is from 95% to 100%, or from 97% to 100%.

The term "patient" refers to organisms to be treated by the methods of the present invention. Such organisms preferably include, but are not limited to, mammals (e.g., murines, simians, equines, bovines, porcines, canines, felines, and the like), and most preferably includes humans.

As used herein, the term "effective amount" refers to the amount of a compound sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

"Therapeutically effective amount" includes an amount of a compound of the invention that is effective when administered alone or in combination to treat the desired condition or disorder. "Therapeutically effective amount" includes an amount of the combination of compounds claimed that is effective to treat the desired condition or disorder. The combination of compounds can be additive and is preferably a synergistic combination. Synergy, as described, for example, by Chou and Talalay, Adv. Enzyme Regul. 1984, 22:27-55, occurs when the effect of the compounds when administered in combination is greater than the additive effect of the compounds when administered alone as a single agent. In general, a synergistic effect is most clearly demonstrated at sub-optimal concentrations of the compounds. Synergy can be in terms of lower incidence of adverse side effects and/or toxicity, increased efficacy, or some other beneficial effect of the combination compared with the individual components.

"Pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of the basic residues. The pharmaceutically acceptable salts include the conventional quaternary ammonium salts of the parent compound formed, for example, from non-toxic inorganic or organic acids. These salts can be prepared in situ in the administration vehicle or the dosage form manufacturing process, or by separately reacting a purified compound of the invention in its free base form with a suitable organic or inorganic acid, and isolating the salt thus formed during subsequent purification. For example, such conventional non-toxic salts include, but are not limited to, those derived from inorganic and organic acids selected from 1,2-ethanedisulfonic, 2-acetoxybenzoic, 2-hydroxyethanesulfonic, acetic, ascorbic, benzenesulfonic, benzoic, bicarbonic, bisulfonic, carbonic, citric, edetic, ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauric, lauryl sulfonic, maleic, malic, mandelic, methanesulfonic, napsylic, naphthylic, nitric, oleic, oxalic, palimitic, pamoic, pantothenic, phenylacetic, phosphoric, polygalacturonic, propionic, salicyclic, stearic, succinic, sulfamic, sulfanilic, sulfuric, tannic, tartaric, toluenesulfonic, and valeric. (See, for example, Berge et al. (1977) "Pharmaceutical Salts", J. Pharm. Sci. 66:1-19.). In certain embodiments, the pharmaceutically acceptable salt is a hydrochloric acid salt. In certain other embodiments, the pharmaceutically acceptable salt is a hydrobromic acid salt.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable carrier" refers to any of the standard pharmaceutical carriers, such as a phosphate buffered saline solution, water, emulsions (e.g., such as oil/water or water/oil emulsions), and various types of wetting agents. The compositions also can include stabilizers and preservatives. For examples of carriers, stabilizers and adjuvants, see e.g., Martin, Remington's Pharmaceutical Sciences, 15th Ed., Mack Publ. Co., Easton, Pa. [1975].

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

As a general matter, if a variable is not accompanied by a definition, then the previous definition of the variable controls.

Finally, the invention may be embodied in other specific forms without departing from the spirit or essential attributes thereof. This invention encompasses all combinations of aspects and embodiments of the invention noted herein. It is understood that any and all aspects of the invention may be taken in conjunction with any other aspects and/or embodiments to describe additional aspects. It is also to be understood that each individual element of the aspects is intended to be taken individually as its own independent aspect. Furthermore, any element of an aspect is meant to be combined with any and all other elements from any aspect to describe an additional aspect.

EXAMPLES

The invention now being generally described, will be more readily understood by reference to the following examples, which are included merely for purposes of illustration of certain aspects and embodiments of the present invention, and are not intended to limit the invention.

Example 1—Preparation of Racemic Deuterated Bupropion, Rac-1-(M-Chlorophenyl)-2-(Tert-Butylamino)-(2-²H)-Propan-1-One

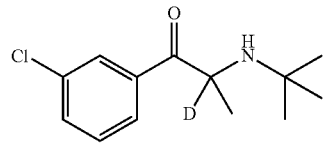 [SMILES: [2H]C(C)(NC(C)(C)C)C(=O)c1cccc(Cl)c1]

rac-1-(m-Chlorophenyl)-2-(tert-butylamino)-(2-²H)-propan-1-one having the chemical structure shown above was prepared by proton/deuterium (H/D) exchange reaction in deuterated potassium phosphate buffer. This compound was then converted to a deuterated trifluoroacetic acid salt. The procedures are described below.

Preparation of 25 mM Deuterated pH=7 Phosphate Buffer:

Deuterated phosphate buffer (100 mM, pH=7) was prepared by dissolving 259.5 mg of potassium phosphate ($K_3PO_4$) in deuterated water ($D_2O$, 12.0 mL) and adding 264 µL 20% deuterium chloride (DCl) in $D_2O$. The resulting 100 mM solution was diluted with 3 times the volume of $D_2O$ to give a 25 mM pH=7 buffer.

Synthesis of rac-1-(m-chlorophenyl)-2-(tert-butylamino)-(2-²H)-propan-1-one

Bupropion, rac-1-(m-chlorophenyl)-2-(tert-butylamino)-propan-1-one (500 mg, 2.09 mmol) was dissolved in 20 mL of 25 mM deuterated pH=7 phosphate buffer. The solution was shaken at room temperature while monitoring H/D exchange by LCMS. After 11 days, LC-MS analysis showed almost complete deuterium incorporation with % D=99.7% at the chiral center. The reaction mixture was washed with a saturated solution of sodium bicarbonate (satd $NaHCO_3$, 80 mL) and ethyl acetate (EtOAc, 400 mL) for just 1 min in order to minimize exposure of the deuterated material to the aqueous solution. The organic layer was quickly separated and dried over sodium sulfate ($Na_2SO_4$). The reaction was repeated starting with 437 mg of bupropion (1.82 mmol) and the organic layers were combined. The solvent (750 mL total) was evaporated in vacuo to give 0.91 g (3.78 mmol) of rac-1-(m-chlorophenyl)-2-(tert-butylamino)-(2-²H)-propan-1-one as a colorless oil. Overall yield: 0.91 g (3.78 mmol, 97%); % D=99.2% at the chiral center.

Synthesis of rac-1-(m-chlorophenyl)-2-(tert-butylamino)-(2-²H)-propan-1-one deuterated trifluoroacetic acid salt rac-1-(m-Chlorophenyl)-2-(tert-butylamino)-(2-²H)-propan-1-one (0.91 g, 3.78 mmol) was dissolved in 25 mL EtOAc. Deuterated trifluoroacetic (d-TFA, 291 µL, 3.78 mmol, 1 eq.) was added at once. Another batch of 32 mg of rac-1-(m-chlorophenyl)-2-(tert-butylamino)-(2-²H)-propan-1-one was treated similarly. The solutions were combined and concentrated to an oil. The residual solvent was removed by dissolving the oil in dichloromethane (DCM, 5 mL) followed by concentration. The procedure was repeated a second time to give the d-TFA salt of rac-1-(m-chlorophenyl)-2-(tert-butylamino)-(2-²H)-propan-1-one as a white solid which was dried under high vacuum for 1 h. Yield:

1.2037 g (3.374 mmol, 86%, 81% over two steps); % D=98.7% at the chiral center.

Example 2—Isolation of Enantiomers A and B of Deuterated Bupropion as Deuterium Chloride Salts from Deuterated Racemic Bupropion Deutero-Trifluoroacetic Acid Salt The d-TFA salt of rac-1-(m-chlorophenyl)-2-(tert-butylamino)-(2-$^2$H)-propan-1-one (1.2 g) was dissolved in 54 mL of a mixture of hexane and 2-propanol (80:20 (v/v)) and separated by HPLC using a Chiralcel OD-H column and a mobile phase system of hexane:2-propanol:2-propylamine: trifluoroacetic acid (90:10:0.025:0.03 (v/v)). Peaks were detected by their UV signal at 275 nm. Pooled fractions of Enantiomer A (first eluting peak, ca. 300 mL) were concentrated under reduced pressure at 25° C. The resultant oily residue was dissolved in EtOAc (38 mL), washed quickly with satd NaHCO$_3$ (0.64 g in 15 mL HPLC quality water; 152 mmol) and water (15 mL) then dried over anhydrous magnesium sulfate (1.2 g). Following filtration and washing the filter cake with additional EtOAc (2×10 mL), the filtrates were concentrated. The DCl salt was formed by dissolving the resulting oil in a mixture of hexane and perdeuterated ($^2$H$_8$)-2-propanol 90:10 (v/v) followed by dropwise addition of a 1 M solution of DCl in diethyl ether (Et$_2$O, 3 mL), and evaporation of the solvents in vacuo. Pooled fractions of Enantiomer B (second eluting peak) were treated separately following the same protocol. After separation, 325 mg (1.164 mmol) and 367 mg (1.314 mmol) of the DCl salts of Enantiomers A and B of deuterium-enriched bupropion were obtained. Overall yield: 792 mg of (R)- and (S)-enantiomers (2.478 mmol, 73%).

Enantiomer A: 99.4% ee; $^1$H NMR (200 MHz, d$_6$-DMSO) δ (ppm): 8.27 (s, 1H), 8.15 (d, 1H), 7.86 (d, 1H), 7.67 (t, 1H), 1.51 (s, 3H), 1.31 (s, 9H); elemental analysis: Anal. Calcd for C$_{13}$H$_{16}$[$^2$H]$_3$ClNO: C, 55.93; H, 6.86; N, 5.02; Cl, 25.40. Found: C, 55.59; H, 6.65; N, 4.94; Cl, 25.19.

Enantiomer B: 96.6% ee; $^1$H NMR (200 MHz, d$_6$-DMSO) δ (ppm): 8.27 (s, 1H), 8.15 (d, 1H), 7.86 (d, 1H), 7.67 (t, 1H), 1.51 (s, 3H), 1.31 (s, 9H); elemental analysis: Anal. Calcd for C$_{13}$H$_{16}$[$^2$H]$_3$ClNO: C, 55.93; H, 6.86; N, 5.02; Cl, 25.40. Found: C, 55.34; H, 6.70; N, 4.76; Cl, 24.31.

Example 3—Determination of Absolute Configuration of 1-(M-Chlorophenyl)-2-(Tert-Butylamino)-(2-$^2$H)-Propan-1-One Enantiomers A and B by their CYP2B6-Catalyzed Metabolism Phase I metabolism of bupropion by CYP2B6 is known to lead to formation of the metabolite hydroxybupropion (Scheme 2). This metabolic transformation has been shown to be stereoselective, i.e., metabolism of (S)-bupropion preferentially leads to formation of (S,S)-hydroxybupropion while (R)-bupropion is mostly metabolized to (R,R)-hydroxybupropion (Coles R. and Kharasch E. D. *Pharm. Res.* 25 (2008), 1405-1411). CYP2B6-catalyzed phase I metabolism of racemic protonated or deuterated bupropion results the (R,R) and (S,S) stereoisomers of hydroxybupropion.

Scheme 2.

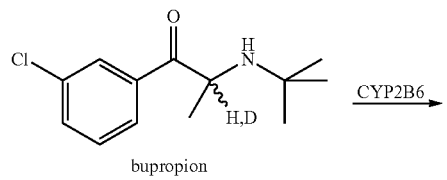

bupropion

-continued

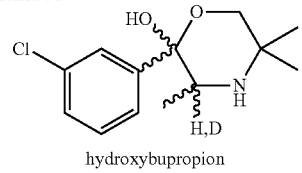

hydroxybupropion

Thus, the deuterium chloride salts of enantiomers A and B of 1-(m-chlorophenyl)-2-(tert-butylamino)-(2-$^2$H)-propan-1-one (40 μM) were incubated at 37° C. in the presence of CYP2B6 Supersomes™ at two CYP2B6 concentrations (2.5 and 25 pmol/mL). Aliquots were taken after 0, 10, and 30 minutes of incubation. Reactions were stopped by addition of a solution containing water, acetonitrile, and formic acid (92:5:3 v/v/v). Control reactions consisted of incubation of the test compounds for 30 minutes with insect control Supersomes™ at protein content equivalent to 2.5 and 25 pmol/mL CYP2B6 to confirm the absence of non-CYP2B6 catalyzed reaction of the test compounds. CYP2B6 Supersomes™ were also incubated for 30 minutes in the absence of test substance to check for microsomal-related material that could interfere with the analysis. Finally the metabolic viability of the Supersomes™ was evaluated by incubation of rac-bupropion as a model substrate (duplicate incubations for 10 min at 25 pmol/mL CYP2B6).

Bupropion enantiomers and the (S,S)- and (R,R)-hydroxybupropion metabolites in the incubation samples were separated by chiral HPLC on a Chiralpak AGP column (100×2 mm, 5 μm, Chiral Technologies, West Chester, Pa.), equipped with a Chiralpak AGP guard column (10×2 mm, Chiral Technologies, West Chester, Pa.) with gradient elution using a mobile phase consisting of solvent A (aqueous 20 mM ammonium formate, pH=5.7) and solvent B (methanol). Peaks were detected by mass spectrometry as their molecular ion (m/z=241 and 257 for deuterated bupropion and deuterated hydroxybupropion, respectively). Enantiomers A and B of deuterated bupropion eluted at 8.3 and 4.0 min while (S,S)- and (R,R)-hydroxybupropion gave peaks at 4.5 and 9.2 min. Enantiomer A was shown to be metabolized to (S,S)-hydroxybupropion while enantiomer B gave (R,R)-hydroxybupropion.

The (S)-absolute configuration was assigned to enantiomer A in Example 2. The (R)-absolute configuration was assigned to enantiomer B in Example 2.

Finally, approximately 82% of (S)-1-(m-chlorophenyl)-2-(tert-butylamino)-(2-$^2$H)-propan-1-one (d-S-bupropion) remained after 30 min of incubation, while the deuterated (R) enantiomer (d-R-bupropion) appeared more stable with approximately 90% remaining after 30 min of incubation.

Example 4—Inhibitory Activity of 1-(M-Chlorophenyl)-2-(Tert-Butylamino)-(2-$^2$H)-Propan-1-One (S)- and (R)-Enantiomers on the Dopamine Transporter and Norepinephrine Transporter The inhibitory activity of the (S)- and (R)-enantiomers of 1-(m-chlorophenyl)-2-(tert-butylamino)-(2-$^2$H)-propan-1-one on the dopamine transporter and norepinephrine transporter were tested. Experimental procedures and results are described below.

Dopamine Transporter (DAT) Inhibition

The inhibitory activity of the (S)- and (R)-enantiomers of 1-(m-chlorophenyl)-2-(tert-butylamino)-(2-$^2$H)-propan-1-one was evaluated in the rat synaptosome assay (Cerep, France). Briefly, each compound was incubated for 15 min at 37° C. with rat striatum synaptosomes in the presence of tritiated dopamine (DA). The uptake of radiolabeled DA by the synaptosomes was measured by scintillation counting as a function of compound concentration. Inhibition of the dopamine transporter is observed when the amount of radio-activity in the synaptosomes is lower in the presence of the test article than in its absence. Analysis of the data was performed using the log(inhibitor) vs. response—variable slope (four parameters) model in GraphPad Prism 6.0 (GraphPad Software, Inc., La Jolla, Calif.), where response is % inhibition (% inhibition=100 [(DA uptake)$_{control}$−(DA uptake)$_{compound}$]/(DA uptake)$_{vehicle}$). Both inhibition curves were characterized by Hill slopes close to 1.

Results of the assay are shown in FIG. 1. The (S)-enantiomer was found to be approximately 10-fold more potent than the (R)-enantiomer at inhibiting uptake of DA in rat striatum synaptosomes. (S)-1-(m-chlorophenyl)-2-(tert-butylamino)-(2-$^2$H)-propan-1-one had an IC$_{50}$=0.42 in this assay, while (R)-1-(m-chlorophenyl)-2-(tert-butylamino)-(2-$^2$H)-propan-1-one had an IC$_{50}$=4.2 µM in this assay.

Norepinephrine Transporter (NET) Inhibition Assay

The inhibitory activity of the (S)- and (R)-enantiomers of 1-(m-chlorophenyl)-2-(tert-butylamino)-(2-$^2$H)-propan-1-one was evaluated in the rat synaptosome assay (Cerep, France). Briefly, compounds were incubated for 20 min at 37° C. with rat hypothalamus synaptosomes in the presence of tritiated norepinephrine (NE). The uptake of radiolabeled NE by the synaptosomes was measured as a function of compound concentration. Inhibition of the transporter is observed when the amount of radioactivity in the synaptosomes is lower in the presence of test article. Analysis of the data was performed using the log(inhibitor) vs. response—variable slope (four parameters) model in GraphPad Prism 6.0 (GraphPad Software, Inc., La Jolla, Calif.), where response is % inhibition (% inhibition=100 [(NE uptake)$_{control}$−(NE uptake)$_{compound}$]/(NE uptake)$_{vehicle}$). Both inhibition curves were characterized by Hill slopes close to 1.

Figure 2:
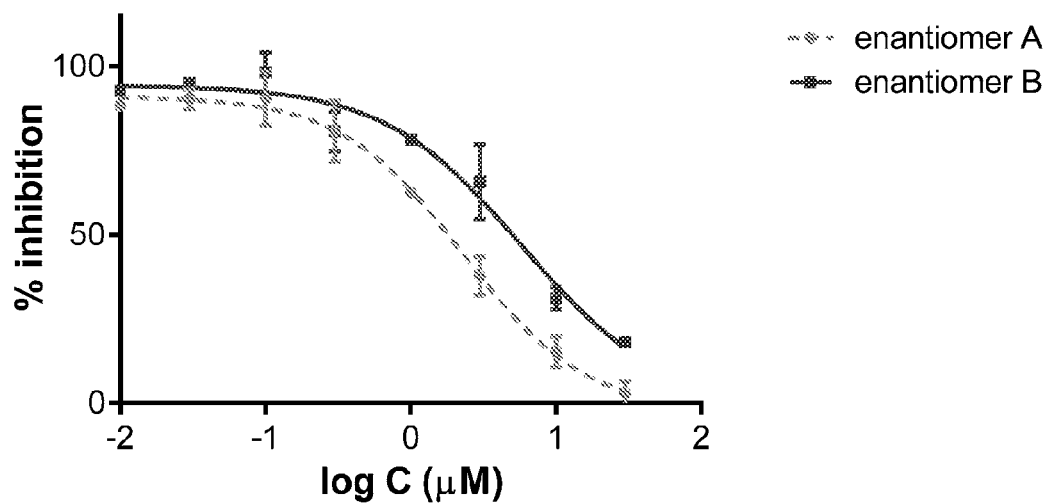
FIG. 2 is line graph and table of results from an assay measuring inhibition of norepinephrine uptake in rat hypothalamus synaptosomes by enantiomers A and B, as defined in Example 2; analysis in GraphPad Prism 6 (log(inhibitor) vs. response—variable slope model); $IC_{50}$ reported in μM; as further described in Example 4 where the abbreviation "Log C" refers to the logarithm of the concentration of the stated enantiomer.

Results of the assay are shown in FIG. 2. The (S)-enantiomer was found to be approximately 2.5-fold more potent than the (R)-enantiomer at inhibiting uptake of NE in rat hypothalamus synaptosomes. (S)-1-(m-chlorophenyl)-2-(tert-butylamino)-(2-$^2$H)-propan-1-one had an IC$_{50}$=2.30 in this assay, while (R)-1-(m-chlorophenyl)-2-(tert-butylamino)-(2-$^2$H)-propan-1-one had an IC$_{50}$=5.76 µM in this assay.

Example 5—Functional Characterization of the Enantiomers of 1-(Meta-Chlorophenyl)-2-(Tert-Butylamino)-(2-$^2$H)-Propan-1-One (Deuterated Bupropion) at Human α7 and α4β2 Nicotinic Acetylcholine Receptors (nAChRs)

Inhibition of human α7 and α4β2 nicotinic acetylcholine receptors by the (S)-enantiomer of 1-(m-chlorophenyl)-2-(tert-butylamino)-(2-$^2$H)-propan-1-one (hereinafter "d-S-bupropion") and the (R)-enantiomer of 1-(m-chlorophenyl)-2-(tert-butylamino)-(2-$^2$H)-propan-1-one (hereinafter "d-R-bupropion") was evaluated. Experimental procedures and results are provided below.

Part I—Experimental Procedure

Evaluation of the antagonist activity of the enantiomers of deuterated bupropion at α7 and α4β2 nicotinic acetylcholine receptors (nAChRs) was carried out in Xenopus Laevis oocytes prepared and injected with the corresponding cDNA using standard procedures. Receptor expression was examined two days after injection. For α4β2 nAChR, the two cDNAs were injected in equimolar amounts. All experiments were performed at 18° C. and cells were superfused with OR2 medium containing 82.5 mM sodium chloride, 2.5 mM potassium chloride, 5 mM HEPES, 1.8 mM calcium chloride, and 1 mM magnesium chloride at pH 7.4. A two-electrode voltage-clamp configuration was used to record currents evoked by acetylcholine addition. Data acquisition and analysis was performed in Matlab (Mathworks, Inc., Natick, Mass.). Statistical analysis was executed in Excel (Microsoft Corp, Redmond, Wash.) or Matlab (Mathwork, Inc., Natick, Mass.). All experiments were carried out using at least 3 oocytes.

Part II—Results

Results from the assay are provided in Table 5 below, which shows data on inhibition of acetylcholine induced current by the enantiomers of deuterated bupropion in Xenopus Laevis oocytes overexpressing α4β2 or α7 nicotinic acetylcholine receptors. The assay results showed that both d-S-bupropion and d-R-bupropion inhibited the two nAChRs tested in a dose-dependent manner. Both d-S-bupropion and d-R-bupropion were more potent antagonists at α4β2 than at α7. d-S-Bupropion was approximately 5-fold more potent than d-R-bupropion at inhibiting the α4β2 receptor. d-S-Bupropion was approximately 1.5-fold less potent than d-R-bupropion at inhibiting α7.

TABLE 5

|  | d-S-bupropion | d-R-bupropion |
| --- | --- | --- |
| IC$_{50}$ α4β2 (µM) | 0.81 | 3.72 |
| IC$_{50}$ α7 (µM) | 43.2 | 28.7 |

Example 6—Behavioral Effects of the (S)- and (R)-Enantiomers of 1-(Meta-Chlorophenyl)-2-(Tert-Butylamino)-(2-$^2$H)-Propan-1-One in Female CD-1 Mice The behavioral effects of the (S)-enantiomer of 1-(m-chlorophenyl)-2-(tert-butylamino)-(2-$^2$H)-propan-1-one (hereinafter "d-S-bupropion") and the behavioral effects of the (R)-enantiomer of 1-(m-chlorophenyl)-2-(tert-butylamino)-(2-$^2$H)-propan-1-one (hereinafter "d-R-bupropion") were evaluated in female CD-1 mice. Experimental procedures and results are provided below.

Part I—Experimental Procedure

Female CD-1 mice (Harlan Laboratories Inc., Indianapolis, Ind.) were randomized to treatment groups (n=7-10 per group) consisting of a single intraperitoneal (i.p.) injection of d-S-bupropion and d-R-bupropion, respectively, at 100, 125, or 150 mg/kg and 10 mL/kg in 0.9% sodium chloride. Individual body weights were used for dose volume calculations. Equal numbers of animals per group were tested each day. After dosing, study animals were housed individually in standard clear Plexiglas mouse cages and observed for a period of 2 h. Animals were also observed 24 h post-dose. During the 2 h observation period, presence or absence of ataxic gait, paralysis, hyperactivity, hypoactivity, and catatonic episodes was recorded. Number, time of onset, duration, and intensity of convulsions were also recorded. Duration of each convulsion was graded as short (1 to 10 s), medium (11 to 30 s), or long (≥31 s). Intensity of convulsion was similarly graded as mild, moderate, or severe. Any animal showing a single episode of severe seizure longer than 1 min or experiencing greater than 40 consecutive episodes of severe convulsions over 1 h or less was euthanized.

Part II—Results

Experimental results are provided in Table 6 below, which shows the number of female CD-1 mice per dose group (in %) experiencing behavioral effects upon intraperitoneal injection of d-S-bupropion (d-S) or d-R-bupropion (d-R) at a dosage of 100, 125, or 150 mg/kg. Intraperitoneal administration of d-S-bupropion resulted in fewer animals experiencing catatonic events than dosing of d-R-bupropion at all dose levels. Hypoactivity was observed in all mice dosed with d-R-bupropion, while hypoactivity was only observed at a high dose of d-S-bupropion. Conversely, hyperactivity was present only in mice administered d-S-bupropion and in decreasing numbers with increasing dose.

TABLE 6

| Behavior Effect | 100 mg/kg | | 125 mg/kg | | 150 mg/kg | |
| --- | --- | --- | --- | --- | --- | --- |
|  | d-S | d-R | d-S | d-R | d-S | d-R |
| convulsions | 40% | 33% | 70% | 60% | 100% | 100% |
| ataxia | 70% | 56% | 89% | 80% | 100% | 90% |
| catatonia | 10% | 78% | 44% | 90% | 80% | 100% |
| hyperactivity | 100% | 0% | 78% | 0% | 20% | 0% |
| hypoactivity | 0% | 100% | 0% | 100% | 80% | 100% |

Example 7—Analysis of Pharmacokinetics of the (S)- and (R)-Enantiomers of 1-(Meta-Chlorophenyl)-2-(Tert-Butylamino)-(2-$^2$H)-Propan-1-One in Comparison with Rac-1-(Meta-Chlorophenyl)-2-(Tert-Butylamino)-Propan-1-One in Mice The pharmacokinetic (PK) profiles of the (S)-enantiomer of 1-(m-chlorophenyl)-2-(tert-butylamino)-(2-$^2$H)-propan-1-one (hereinafter "d-S-bupropion") and the (R)-enantiomer of 1-(m-chlorophenyl)-2-(tert-butylamino)-(2-$^2$H)-propan-1-one (hereinafter "d-R-bupropion") were evaluated in comparison with racemic-1-(m-chlorophenyl)-2-(tert-butylamino)-propan-1-one (hereinafter "h-rac-bupropion") in mice. Experimental procedures and results are provided below.

Part I—Experimental Procedure

The PK profiles of d-S-bupropion and d-R-bupropion were compared to that of h-rac-bupropion in mice. As appreciated, h-rac-bupropion is a 1:1 mixture of the two protonated enantiomers h-S-bupropion and h-R-bupropion. Male C57BL/6 mice were administered by oral gavage d-S-bupropion, d-R-bupropion, or h-rac-bupropion at 75, 75, and 150 mg/kg respectively, to adjust for levels of the enantiomers in h-rac-bupropion. Animals were euthanized at preset time points (n=3 per time point). Plasma samples were collected and analyzed by chiral HPLC/MS-MS for the enantiomers of protonated and deuterated bupropion, i.e., h-S-bupropion, h-R-bupropion, d-S-bupropion, and d-R-bupropion, and the active diastereomers of protonated and deuterated metabolite hydroxybupropion, i.e., SS- and RR-hydroxybupropion, respectively. The HPLC method was similar to that described above in Example 3. Quantitative data was analyzed in Excel (Microsoft Corp, Redmond, Wash.) using the PKSolver add-in (version 2, as described by Zhang et al. in *Comput Methods Programs Biomed* 99 (2010) 306-314) to determine PK parameters.

Part II—Results

Figure 3:
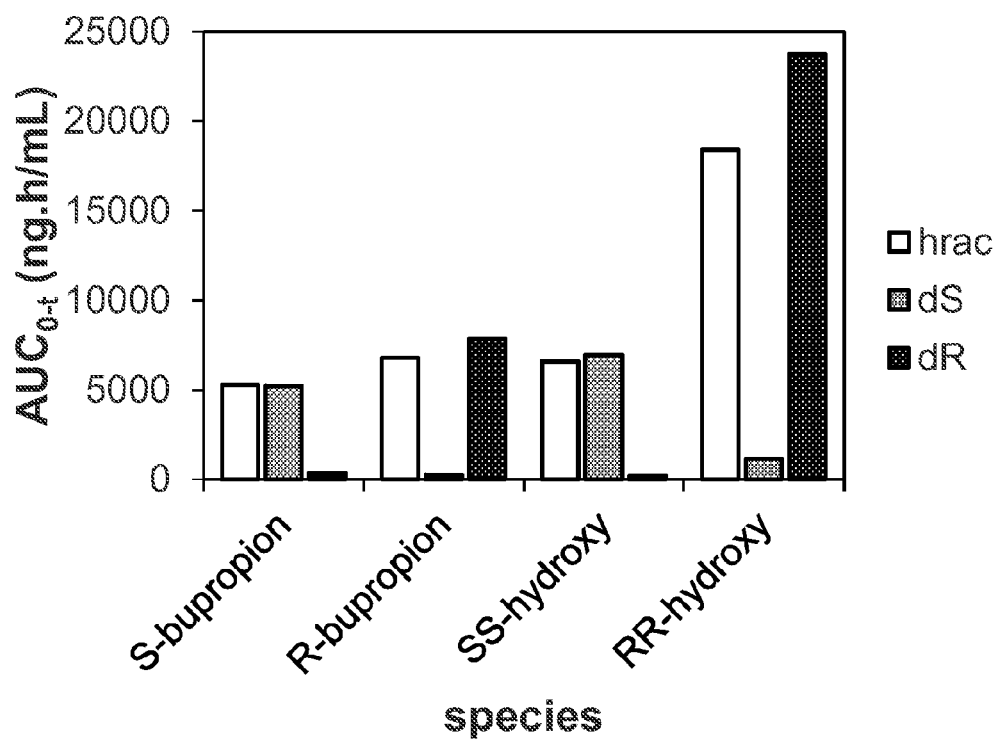
FIG. 3 is a bar graph showing relative exposure (AUC) of bupropion enantiomers (S-bupropion and R-bupropion), and the two observed hydroxybuproprion diastereomeric metabolites (abbreviated as "SS-hydroxy" and "RR-hydroxy") after oral gavage of 150 mg/kg h-rac-bupropion (hollow bar), 75 mg/kg d-S-bupropion (light pattern bar), and 75 mg/kg d-R-bupropion (dark pattern bar) in C57BL/6 male mice, as further described in Example 7. As appreciated, the amount of "S-bupropion" reported in FIG. 3 following administration of deuterium-enriched bupropion is deuterium-enriched S-bupropion. Similarly, (i) the amount of "R-bupropion" reported in FIG. 3 following administration of deuterium-enriched bupropion is deuterium-enriched R-bupropion, (ii) the amount of "SS-hydroxy" reported in FIG. 3 following administration of deuterium-enriched bupropion is deuterium-enriched SS-hydroxybupropion metabolite, and (iii) the amount of "RR-hydroxy" reported in FIG. 3 following administration of deuterium-enriched bupropion is deuterium-enriched RR-hydroxybupropion metabolite.

Experimental results are shown in FIG. 3 and Tables 7 and 8. FIG. 3 graphically compares exposure to each enantiomer of bupropion as the sum of both protonated and deuterated isotopomers, and the exposure to each of the two observed diastereomers of hydroxybupropion as the sum of both protonated and deuterated isotopomers, after oral gavage. Tables 7 and 8 collectively provide data on elimination half-lives, $t_{1/2}$, and area under the curve, $AUC_{0-t}$, for the enantiomers of protonated and deuterated bupropion and the diastereomers of protonated and deuterated hydroxybupropion metabolites obtained by analysis of PK data collected in male C57BL/6 mice after oral gavage with 150 mg/kg h-rac-bupropion, 75 mg/kg d-S-bupropion or 75 mg/kg d-R-bupropion. The abbreviations hR, hS, dR, dS, hRR, hSS, dRR, and dSS stand for h-R-bupropion, h-S-bupropion, d-R-bupropion, d-S-bupropion, h-RR-hydroxybupropion, h-SS-hydroxybupropion, d-RR-hydroxybupropion, and d-SS-hydroxybupropion, respectively.

When mice were gavaged with each deuterated enantiomer of bupropion, exposure to the corresponding enantiomer of bupropion or hydroxybupropion was unchanged compared to what was observed after administration of the racemate, h-rac-bupropion. Animals gavaged with d-S-bupropion showed almost exclusive exposure to (S)-bupropion and (S,S)-hydroxybupropion and very little (R)-bupropion and (R,R)-hydroxybupropion. Likewise, animals administered d-R-bupropion exhibited very limited exposure to (S)-bupropion and (S,S)-hydroxybupropion. Limited deuterium/hydrogen exchange was evidenced by the minimal exposure to the protonated enantiomers of bupropion and diastereomers of hydroxybupropion in mice administered either d-R-bupropion or d-S-bupropion.

In all 3 dose groups, exposure to the diastereomers of hydroxybupropion was higher than to the enantiomers of bupropion (RR/R~3 and SS/S~1.3). Elimination half-lives of the enantiomers of bupropion and the diastereomers of hydroxybupropion were also unaffected by deuteration.

TABLE 7

| Compound | $t_{1/2}$ (h) | | | | | | | |
| --- | --- | --- | --- | --- | --- | --- | --- | --- |
|  | hR | hS | hRR | hSS | dR | dS | dRR | dSS |
| h-rac-bupropion | 1.1 | 1.2 | 4.7 | 2.6 | — | — | — | — |
| d-S-bupropion | 1.4 | 1.1 | — | — | — | 0.9 | — | 2.2 |
| d-R-bupropion | 1.7 | — | 2.5 | — | 1.7 | — | 2.5 | — |

TABLE 8

| Compound | $AUC_{0-t}$ (ng · h/mL) | | | | | | | |
| --- | --- | --- | --- | --- | --- | --- | --- | --- |
|  | hR | hS | hRR | hSS | dR | dS | dRR | dSS |
| h-rac-bupropion | 6798 | 5265 | 18393 | 6591 | — | — | — | — |
| d-S-bupropion | 269 | 469 | 1129 | 395 | — | 4763 | — | 6545 |
| d-R-bupropion | 496 | 340 | 1685 | 169 | 7342 | — | 22059 | — |

INCORPORATION BY REFERENCE

All references listed herein are individually incorporated in their entirety by reference.

EQUIVALENTS

Numerous modifications and variations of the invention are possible in light of the above teachings. It is therefore to be understood that within the scope of the appended claims, the invention may be practiced otherwise that as specifically described herein.

What is claimed is:

1. A method of treating obesity, comprising administering to a patient in need thereof a therapeutically effective amount of a deuterium-enriched compound of Formula I-A having an optical purity of at least 75% enantiomeric excess to treat the obesity, wherein Formula I-A is represented by:

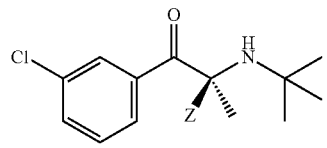

(I-A)

or a pharmaceutically acceptable salt thereof, wherein Z is H or D, provided that the abundance of deuterium in Z is at least 60%.

2. A method of treating obesity, comprising administering to a patient in need thereof a therapeutically effective amount of a deuterium-enriched compound of Formula II-A having an optical purity of at least 75% enantiomeric excess to treat the obesity, wherein Formula II-A is represented by:

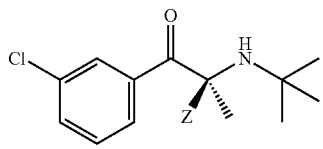

(II-A)

or a pharmaceutically acceptable salt thereof, wherein Z is H or D, provided that the abundance of deuterium in Z is at least 60%.

3. The method of claim 2, wherein the abundance of deuterium in Z is at least 90%.

4. The method of claim 3, wherein the compound has an enantiomeric excess of at least 85%.

5. The method of claim 2, wherein the compound is:

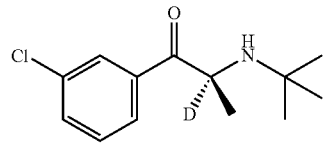 [SMILES: [2H][C@@](C)(NC(C)(C)C)C(=O)c1cccc(Cl)c1]

or a pharmaceutically acceptable salt thereof, each having an optical purity of at least 90% enantiomeric excess.

6. The method of claim 2, wherein the compound is:

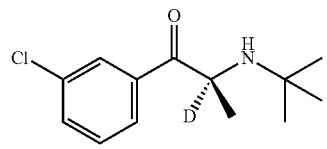 [SMILES: [2H][C@@](C)(NC(C)(C)C)C(=O)c1cccc(Cl)c1]

having an optical purity of at least 90% enantiomeric excess.

7. The method of claim 2, wherein the compound is:

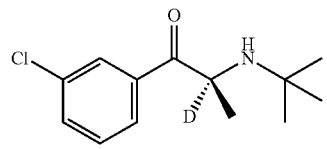 [SMILES: [2H][C@@](C)(NC(C)(C)C)C(=O)c1cccc(Cl)c1]

or pharmaceutically acceptable salt thereof, each having an optical purity of at least 95% enantiomeric excess.

8. The method of claim 2, wherein the compound is:

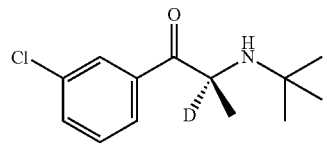 [SMILES: [2H][C@@](C)(NC(C)(C)C)C(=O)c1cccc(Cl)c1]

having an optical purity of at least 95% enantiomeric excess.

9. The method of claim 5, wherein the compound is administered at a daily dose in the range of about 50 mg to 75 mg, 75 mg to 100 mg, 100 mg to 125 mg, 125 mg to 150 mg, 150 mg to 175 mg, 175 mg to 200 mg, 200 mg to 225 mg, 225 mg to 250 mg, 250 mg to 275 mg, or 275 mg to 300 mg.

* * * * *

UNITED STATES PATENT AND TRADEMARK OFFICE
CERTIFICATE OF CORRECTION

PATENT NO. : 9,732,031 B2
APPLICATION NO. : 15/103144
DATED : August 15, 2017
INVENTOR(S) : Sheila DeWitt et al.

Page 1 of 1

It is certified that error appears in the above-identified patent and that said Letters Patent is hereby corrected as shown below:

In the Claims

Column 37, Lines 39-45 Claim 2, replace " 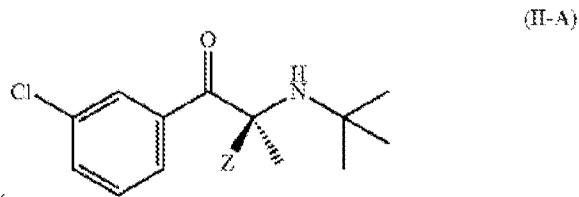 " with

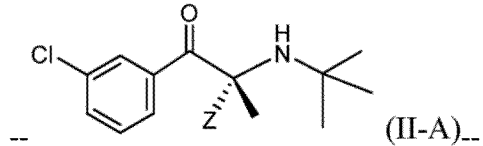 --

Signed and Sealed this
Tenth Day of November, 2020

Andrei Iancu
*Director of the United States Patent and Trademark Office*